(12) United States Patent
Carstens

(10) Patent No.: US 8,262,638 B2
(45) Date of Patent: *Sep. 11, 2012

(54) DIAPER AND ABSORBENT ARTICLE

(75) Inventor: Jerry Edward Carstens, West Chester, OH (US)

(73) Assignee: RUSL, LLC, West Chester, OH (US)

(*) Notice: Subject to any disclaimer, the term of this patent is extended or adjusted under 35 U.S.C. 154(b) by 144 days.

This patent is subject to a terminal disclaimer.

(21) Appl. No.: 12/871,521

(22) Filed: Aug. 30, 2010

(65) Prior Publication Data

US 2010/0324526 A1    Dec. 23, 2010

Related U.S. Application Data

(63) Continuation of application No. 11/562,975, filed on Nov. 22, 2006, now Pat. No. 7,785,311.

(51) Int. Cl.
*A61F 13/15* (2006.01)

(52) U.S. Cl. ............................ 604/396; 604/402

(58) Field of Classification Search ......... 604/394–396, 604/400–402
See application file for complete search history.

(56) References Cited

U.S. PATENT DOCUMENTS

| | | | |
|---|---|---|---|
| 2,792,698 A | 5/1957 | Hampp |
| 2,837,095 A | 6/1958 | Stevenson |
| 3,368,563 A | 2/1968 | Scheier |
| 3,929,135 A | 12/1975 | Thompson |
| 4,324,245 A | 4/1982 | Mesek et al. |
| 4,342,314 A | 8/1982 | Radel et al. |
| 4,424,809 A | 1/1984 | Yovankin |
| 4,463,045 A | 7/1984 | Ahr et al. |
| 4,527,403 A | 7/1985 | Fullbright et al. |
| 4,687,478 A | 8/1987 | Van Tillburg |
| 4,777,073 A | 10/1988 | Sheth |
| 4,990,147 A | 2/1991 | Freeland |
| 5,006,394 A | 4/1991 | Baird |
| 5,207,663 A | 5/1993 | McQueen |
| 5,267,992 A | 12/1993 | Van Tilburg |
| 5,354,400 A | 10/1994 | Lavash et al. |
| 5,415,650 A | 5/1995 | Sigl et al. |
| 5,562,648 A | 10/1996 | Peterson |
| 5,607,760 A | 3/1997 | Roe |
| 5,609,587 A | 3/1997 | Roe |
| 5,624,426 A | 4/1997 | Roe et al. |
| 5,671,615 A | 9/1997 | Kjaergaard et al. |
| 5,674,216 A | 10/1997 | Buell et al. |
| 5,676,652 A | 10/1997 | Hunter et al. |
| 5,690,627 A | 11/1997 | Clear et al. |
| 5,782,819 A | 7/1998 | Tanzer et al. |
| 6,120,485 A | 9/2000 | Gustafsson et al. |
| 6,156,024 A | 12/2000 | Schulte et al. |
| 6,183,458 B1 | 2/2001 | Ahlstrand et al. |
| 6,287,169 B1 | 9/2001 | Willms et al. |
| 6,290,979 B1 | 9/2001 | Roe et al. |

(Continued)

*Primary Examiner* — Lynne Anderson

(74) *Attorney, Agent, or Firm* — Hasse & Nesbitt LLC; Donald E. Hasse

(57) ABSTRACT

A diaper for holding an absorbent article in close bodily contact in the crotch region of the wearer. The diaper comprises a front region, a crotch region having a specified Crotch Holding Force, and a rear region. The crotch region of the diaper typically is elastically extensible in both the longitudinal and lateral directions. The diaper provides an upward holding force against the absorbent article in the crotch region to hold the article in close bodily contact. A system comprising the diaper and an absorbent article for use therewith, and a method for holding such an article in close bodily contact by wearing the diaper, is also disclosed.

27 Claims, 12 Drawing Sheets

U.S. PATENT DOCUMENTS

| | | |
|---|---|---|
| 6,346,097 B1 | 2/2002 | Blaney |
| 6,375,646 B1 | 4/2002 | Widlund et al. |
| 6,393,621 B1 | 5/2002 | Redwine et al. |
| 6,551,292 B1 | 4/2003 | D'Acchioli et al. |
| 6,570,053 B2 | 5/2003 | Roe et al. |
| 6,582,411 B1 | 6/2003 | Carstens et al. |
| 6,595,977 B1 | 7/2003 | Luizzi, Jr. et al. |
| 6,602,233 B1 | 8/2003 | Palumbo et al. |
| 6,605,071 B1 | 8/2003 | Gray et al. |
| 6,613,034 B2 | 9/2003 | Nozaki et al. |
| 6,613,175 B1 | 9/2003 | Moscherosch et al. |
| 6,616,649 B1 | 9/2003 | Ismail |
| 6,702,801 B2 | 3/2004 | Van Gompel et al. |
| 6,713,660 B1 | 3/2004 | Roe et al. |
| 6,726,668 B2 | 4/2004 | Underhill et al. |
| 6,761,710 B2 | 7/2004 | D'Acchioli et al. |
| 6,773,424 B2 | 8/2004 | Heyrman et al. |
| 6,969,378 B1 | 11/2005 | Vukos et al. |
| 7,018,368 B2 | 3/2006 | VanGompel et al. |
| 7,056,411 B2 | 6/2006 | Desai et al. |
| 7,223,818 B2 | 5/2007 | Autran et al. |
| 7,273,476 B2 | 9/2007 | Mueller et al. |
| 7,458,961 B2 | 12/2008 | Carstens |
| 7,462,173 B2 | 12/2008 | Carstens |
| 7,481,801 B2 | 1/2009 | Carstens |
| 7,537,587 B2 | 5/2009 | Carstens |
| 7,614,399 B2 | 11/2009 | Carstens |
| 7,785,311 B2 * | 8/2010 | Carstens ............ 604/385.22 |
| 7,789,867 B2 | 9/2010 | Carstens |
| 7,803,147 B2 | 9/2010 | Carstens |
| 7,846,145 B2 | 12/2010 | Carstens |
| 7,867,211 B2 | 1/2011 | Carstens |
| 8,099,794 B2 | 1/2012 | Carstens |
| 2003/0181884 A1 | 9/2003 | Carstens et al. |
| 2003/0229327 A1 | 12/2003 | Imsangjan et al. |
| 2004/0060649 A1 | 4/2004 | Van Gompel et al. |
| 2004/0127881 A1 | 7/2004 | Stevens et al. |
| 2004/0193133 A1 | 9/2004 | Desai et al. |
| 2005/0090795 A1 | 4/2005 | Coleman |
| 2005/0096623 A1 | 5/2005 | Nhan et al. |
| 2005/0256489 A1 | 11/2005 | Sawyer et al. |
| 2006/0004341 A1 | 1/2006 | Olson et al. |
| 2006/0004342 A1 | 1/2006 | Sawyer et al. |
| 2006/0253093 A1 | 11/2006 | Beck et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2007/0093771 A1 | 4/2007 | Arizti et al. |
| 2007/0102461 A1 | 5/2007 | Carstens |
| 2007/0106237 A1 | 5/2007 | Carstens |
| 2007/0106350 A1 | 5/2007 | Carstens |
| 2007/0106352 A1 | 5/2007 | Carstens |
| 2007/0106353 A1 | 5/2007 | Carstens |
| 2007/0106354 A1 | 5/2007 | Carstens |
| 2007/0106355 A1 | 5/2007 | Carstens |
| 2007/0106356 A1 | 5/2007 | Carstens |
| 2007/0142816 A1 | 6/2007 | Carstens |
| 2007/0287348 A1 | 12/2007 | Autran et al. |
| 2008/0119815 A1 | 5/2008 | Carstens |
| 2009/0030392 A1 | 1/2009 | Kanai et al. |
| 2010/0094240 A9 | 4/2010 | Desai et al. |
| 2010/0324522 A1 | 12/2010 | Carstens |
| 2010/0324525 A1 | 12/2010 | Carstens |
| 2010/0324526 A1 | 12/2010 | Carstens |
| 2011/0092945 A1 | 4/2011 | Carstens |

* cited by examiner

DIAPER AND ABSORBENT ARTICLE

CROSS-REFERENCE TO RELATED APPLICATION

This application is a continuation of U.S. patent application Ser. No. 11/562,975, filed on Nov. 22, 2006, now U.S. Pat. No. 7,785,311, incorporated herein by reference.

FIELD OF THE INVENTION

The present invention relates to a reusable textile diaper for holding an absorbent article in close bodily contact in the crotch region of the wearer. More particularly, the invention relates to such a diaper for an absorbent article having a compatible shape and size, such as a urine and/or BM pad, bag, or other absorbent device. The invention also relates to a system comprising the diaper and an absorbent article for use therewith, and a method for holding such an absorbent article in close bodily contact by wearing the diaper.

BACKGROUND OF THE INVENTION

Disposable absorbent articles are commercially available in a wide variety of configurations for absorbing and retaining urine and feces. Unfortunately, such absorbent articles may leak along their periphery due to poor fit or improper placement. Such leakage frequently results in soiling of a wearer's clothing or bedding.

While there are many patents and applications disclosing various garments and systems for holding absorbent articles against the body, there is a continuing need for a reusable textile diaper capable of holding an absorbent article in close bodily contact in the crotch region to provide improved leakage protection and wearer comfort.

SUMMARY OF THE INVENTION

The present invention relates to a diaper for holding an absorbent article in close bodily contact in the crotch region, said diaper having a longitudinal centerline defining a longitudinal direction and a lateral centerline defining a lateral direction, said diaper comprising:
1) a front region;
2) a crotch region attached to the front region, said crotch region having a Crotch Holding Force (CHF-4.0) of greater than about 0.1 kgf and a Crotch Holding Force (CHF-5.5) of less than about 1.0 kgf; and
3) a rear region attached to the crotch region, said rear region capable of cooperating with the front region to provide an adjustable waistband.

The invention also relates to a diaper for holding an absorbent article in close bodily contact in the crotch region, said diaper having a longitudinal centerline defining a longitudinal direction and a lateral centerline defining a lateral direction, said diaper comprising:
1) a front region;
2) a crotch region attached to the front region, said crotch region having a Crotch Holding Force (CHF-4.0) of greater than about 0.1 kgf and a Crotch Holding Force (CHF-2.0) of less than about 1.0 kgf; and
3) a rear region attached to the crotch region, said rear region comprising at least two fastening systems that cooperate with the front region to provide an adjustable waistband.

In another aspect, the invention relates to a diaper for holding an absorbent article in close bodily contact in the crotch region, said diaper having a longitudinal centerline defining a longitudinal direction and a lateral centerline defining a lateral direction, said diaper comprising:
a) a front region;
b) a crotch region attached to the front region, said crotch region having a first opening located at the anus of an individual when the article is worn and a second opening located at the urethral opening when the article is worn, and having a Crotch Holding Force (CHF-4.0) of greater than about 0.1 kgf and a Crotch Holding Force (CHF-2.0) of less than about 1.0 kgf; and
c) a rear region attached to the crotch region, said rear region capable of cooperating with the front region to provide an adjustable waistband.

DETAILED DESCRIPTION OF THE INVENTION

Figure 1:
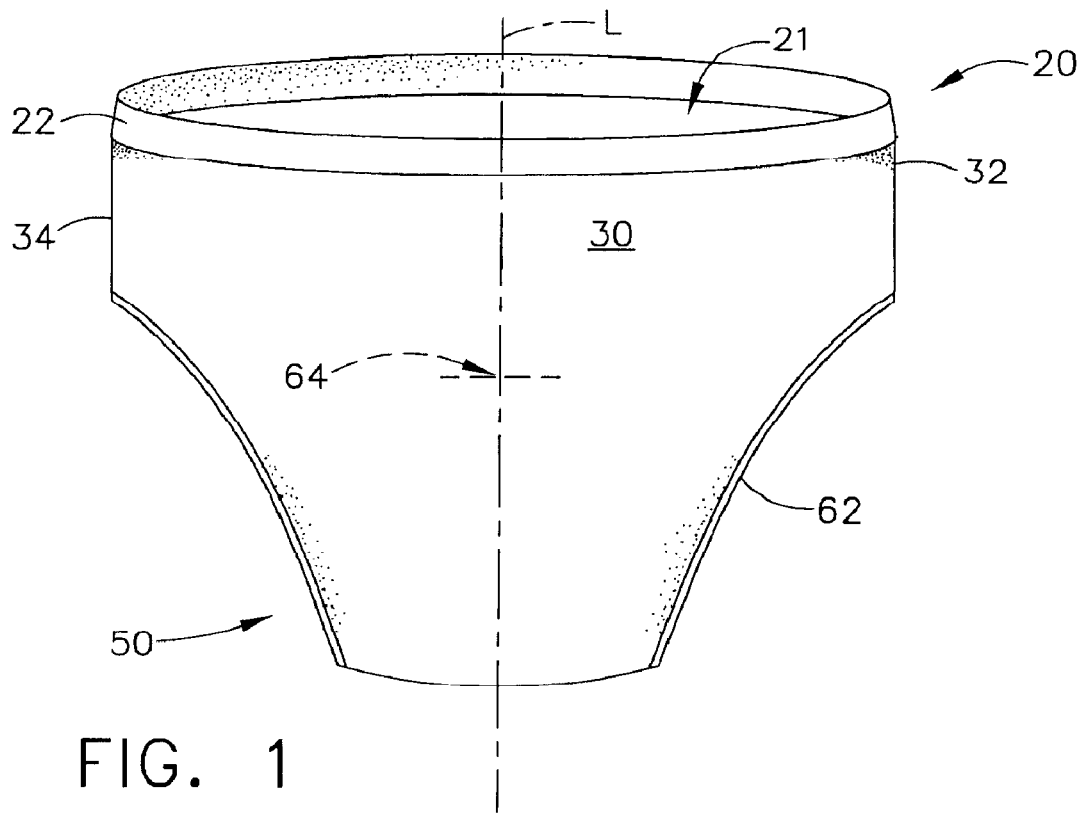
FIG. 1 is a front view of a pull-on diaper of the invention.

The diaper of the invention is suitable for holding a compatible article, typically an absorbent article, in close bodily contact in the crotch region of the wearer. In one embodiment, the diaper is intended for use with urinary and/or BM absorbent articles, such as pads, diaper inserts, and the like. In still another embodiment, the diaper is intended for use with a disposable fluid management device comprising a bag, such as a urine or BM absorbent device. The diaper may also be used with an article comprising a lotion coating, a skin care composition, or a therapeutic composition that is partially transferable to the wearer's skin, or a sensor operatively connected to the article. The absorbent or other article herein typically has a compatible shape and size so that it fits within the crotch region of the wearer.

While not intending to be limited by theory, it is believed that the diaper provides an upward holding force against the article in the crotch region to hold the absorbent article in close bodily contact when the diaper is worn. The diaper thus holds the absorbent article in close bodily contact throughout a range of wearer motions, often providing improved performance (e.g., less leakage from the absorbent article). Additionally, when the diaper and absorbent article are designed and coordinated to work together, the resulting system can be optimized to provide consumer benefits such as leakage prevention, wearing comfort, stay-in-place performance, correct placement, discreetness, and/or cost effectiveness.

The invention also relates to a system comprising the diaper and a compatible article, and a method for holding such an article in close bodily contact in the crotch region by wearing the diaper. The article typically is an absorbent article comprising a liquid pervious side, a liquid impervious side opposite the liquid pervious side, and an absorbent component between the liquid pervious side and the liquid impervious side. The liquid pervious side and the liquid impervious side of the article are arranged to form a unitary structure. The article has a compatible size and shape, and is capable of being held in close bodily contact in the crotch region by the diaper. Compatible absorbent articles include incontinent pads, fluid collection bags, and other devices. Typically, the article and the diaper are designed and coordinated to work together and provide improved performance, comfort and/or fit of the article.

The system of the invention comprises at least one absorbent article in combination with the diaper. The absorbent article and diaper of this system may be packaged in a common, bundled, coordinated, or associated package or packages, and may be sold as a kit, for example a diaper kit.

As used herein, the term "absorbent article" refers to articles that are placed against or in proximity to the body in the wearer's crotch region to acquire, absorb, and contain the various exudates discharged from the body. The term "absorbent article" is intended to include diaper inserts, sanitary pads, incontinence pads, BM pads, fluid collection bags, urine collection bags, feces collection bags (i.e., BM collection bags), and other absorbent articles worn in the crotch region.

The term "BM" (i.e., bowel movement) refers to various fecal exudates that are discharged from the anus. BM pads and BM management devices refer to absorbent articles worn adjacent to the anus region that are intended to absorb and contain the various fecal exudates that are discharged from the body.

The term "disposable" refers to structures that are intended to be discarded after a single use or a few uses (i.e., they are not intended to be cleaned, laundered or otherwise restored and/or reused after use). Such structures may be recycled, composted or otherwise disposed of in an environmentally compatible manner. While the articles described herein are typically disposable, they may be designed to be cleaned, laundered, restored and/or reused many times.

The term "crotch region" refers to the external genitalia and anus regions.

The term "gluteal groove" refers to the crevice between the buttocks (gluteus maximi) extending upwardly from the perineum.

The terms "fluid", "liquid" and the like are intended to be interchangeable and refer to materials that are in a liquid state at a temperature of about 38° C.

As noted above, the invention provides a diaper that holds an article, particularly an absorbent article, against a wearer's body in the crotch region. With a conventional diaper, the crotch region typically does not hold and maintain the absorbent article in close bodily contact. For example, the article may sag when the wearer's legs are brought together and when the user moves. On the other hand, the diaper of the invention holds the article substantially against the crotch region. The diaper typically maintains the upward force against the article throughout a range of body motions so that the article is held in close bodily contact. The close bodily contact generally results in improved performance (e.g., less leakage). Moreover, the diaper is comfortable to wear notwithstanding the close conformity of the diaper and article to the wearer's body. It is believed that the sufficient and comfortable upward holding force provided by the crotch region of the diaper against the article is due at least in part to the force exerted radially and axially by the stretch material used. The crotch region can be characterized as having a relatively low Crotch Holding Force value at a given extension distance, when measured as described herein. In contrast, conventional diapers have often attempted to conform an absorbent article to the crotch area by using materials of relatively low stretch and high stretch modulus.

Figure 2:
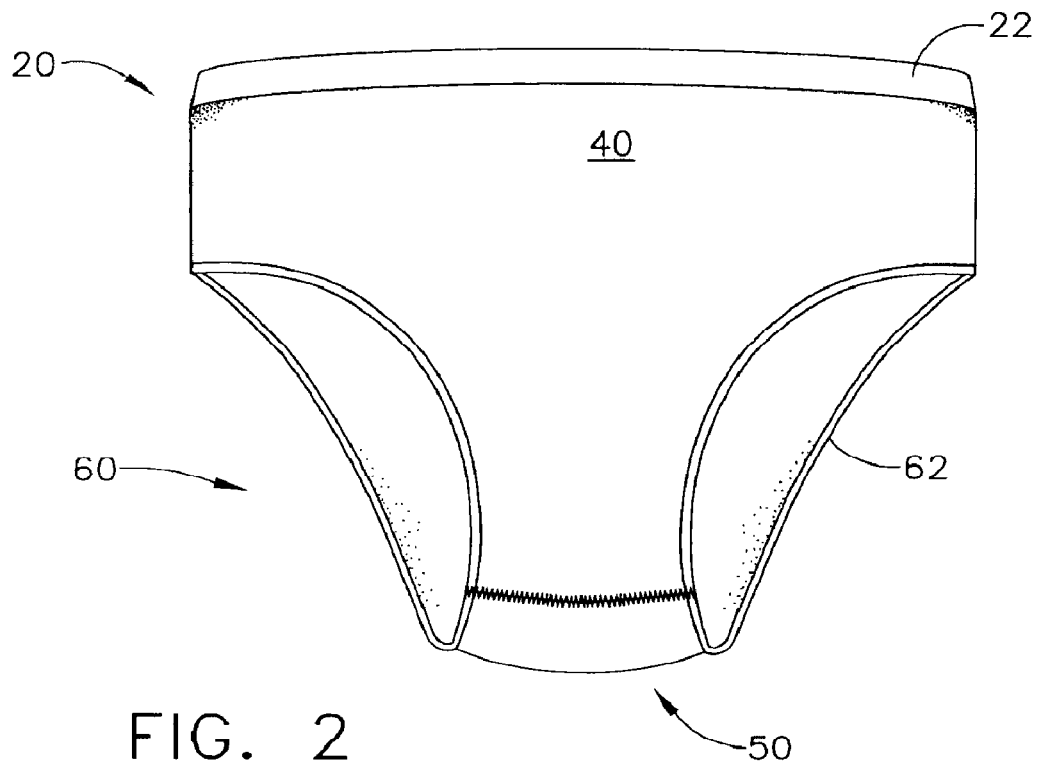
FIG. 2 is a rear view of the pull-on diaper shown in FIG. 1.
Figure 16:
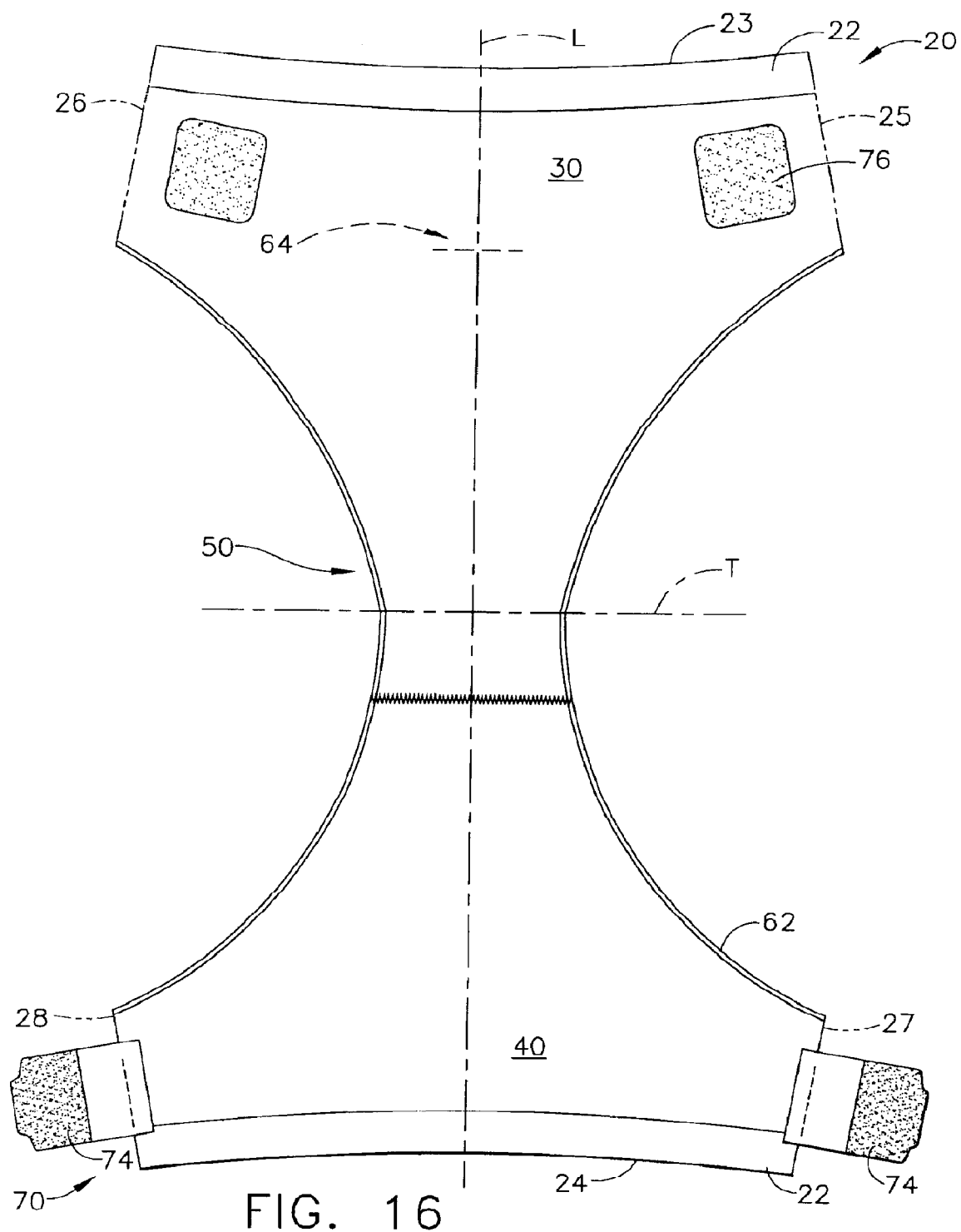
FIG. 16 is a plan view of a diaper of the invention comprising fastening systems.
Figure 18:
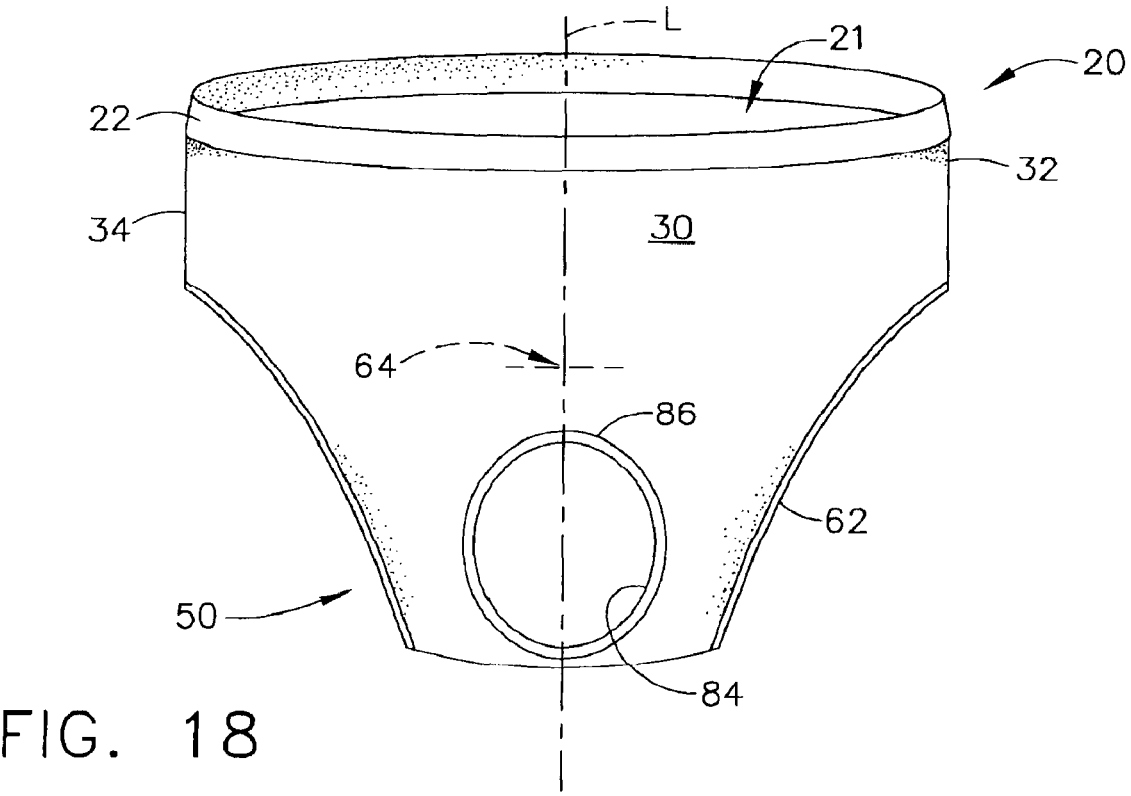
FIG. 18 is a front view of a diaper of the invention comprising an opening at the urethral opening when the diaper is worn.

While the present invention encompasses a wide variety of diaper designs and compatible absorbent articles, it will often be described in terms of a diaper comprising a material of relatively high stretch and low stretch modulus, used in conjunction with an article such as an absorbent pad. FIGS. 1 and 2 show front and rear views of one diaper embodiment of the invention. FIG. 18 shows a front view of another diaper embodiment of the invention. Both diaper embodiments comprise a front region 30, a crotch region 50 attached to the front region, and a rear region 40 attached to the front and crotch regions. The front and rear regions are capable of cooperating to provide an adjustable waistband, such as elasticized waistband 22. The diaper is thus provided with a waist opening 21 that allows entry into the diaper. The front, crotch and rear regions cooperate to provide a pair of leg openings 60. The crotch region extends between the front region and the rear region and to side elastics 62 attached to the leg openings. Typically, the front, rear, and crotch regions are elastic in the lateral and longitudinal directions. In these diaper embodiments, the front and rear regions are connected to provide a "pull-on" type diaper. In another diaper embodiment shown in FIG. 16, the rear region comprises at least two fastening systems that cooperate with the front region to provide an adjustable waistband in an "hour-glass" diaper configuration. Specifically, in the embodiment shown in FIG. 16, the fastening system 70 comprises mechanical fastening tabs 74 attached to the rear region and configured to engage with a second fastening component 76 attached to the front region.

Figure 3:
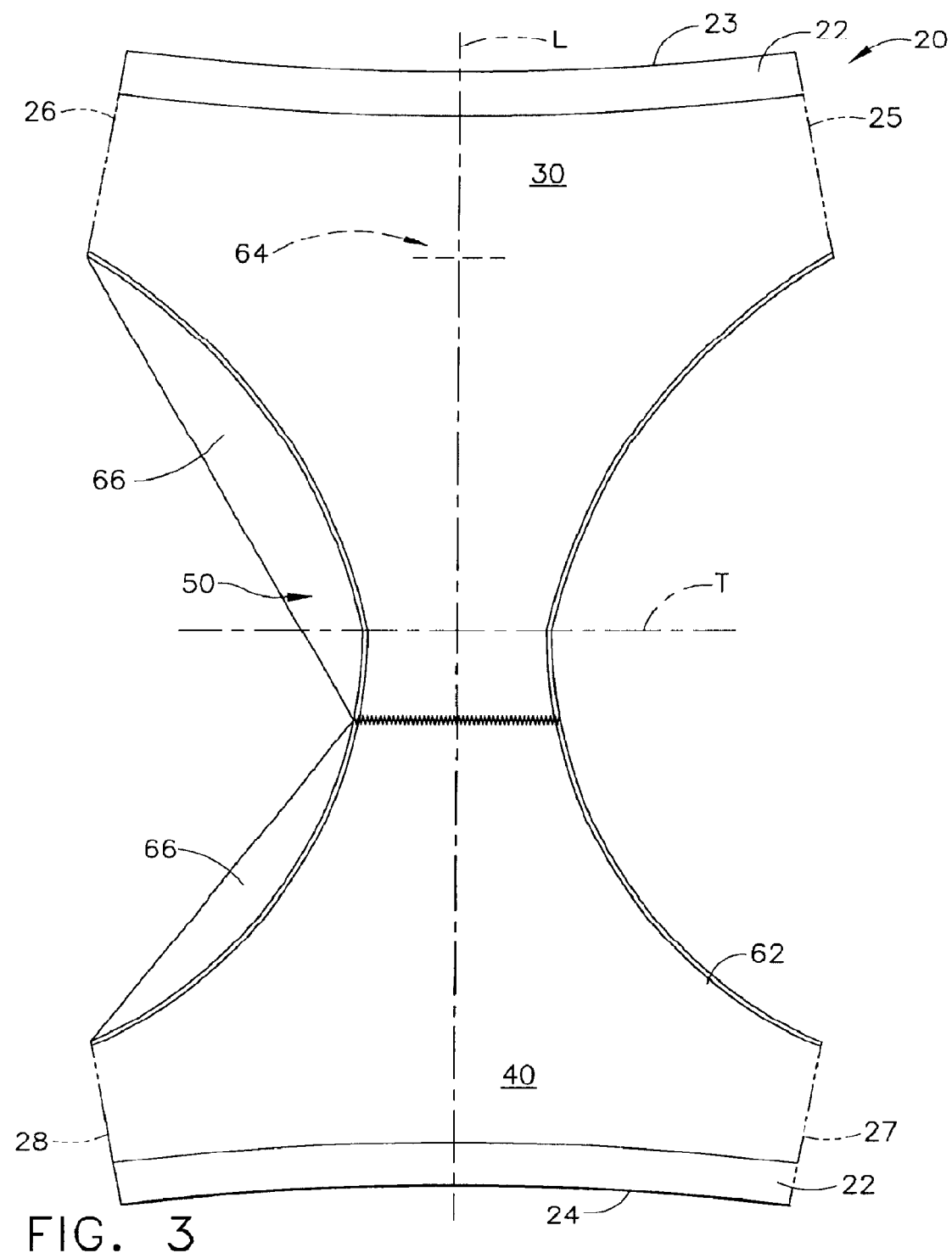
FIG. 3 is a plan view of the pull-on diaper of FIG. 1 that has been opened at the sides, with the elastic components pulled flat, and further comprising an extension or panel on one side of the diaper.

FIG. 3 shows the diaper 20 in a full flat out position wherein each of the sides 32 and 34 has been opened and elastic components have been pulled flat. FIG. 3 can also be considered to be a plan view of one embodiment of the diaper. The diaper has a longitudinal centerline L and a lateral centerline T. The term "longitudinal" refers to a line, axis or direction in the plane of the diaper that is generally aligned with (e. g., approximately parallel to) a vertical plane that bisects a standing wearer into left and right body halves when the diaper is worn. The term "lateral" refers to a line, axis or direction that lies within the plane of the diaper that is generally perpendicular to the longitudinal direction. The diaper typically is symmetric about the longitudinal centerline L and asymmetric about the lateral centerline T.

The diaper 20 can comprise woven, nonwoven (with stretch incorporated as known in the art) or knit fabrics, but typically comprises a knit fabric. Other materials having the requisite mechanical properties are also suitable. The diaper may be durable or disposable, but typically is disposed of after a period of time (e.g., about 1 to 3 months) when it begins to lose elasticity or otherwise shows wear. When the diaper is a knit fabric, the mechanical properties of the various components can be provided by a combination of the knit pattern used for a particular component and the yarns that are used. In one embodiment, the stretch properties of the crotch region of the diaper are derived from circular knit materials known in the art. In one embodiment, the front region, the crotch region, and the rear region are wholly knit. The diaper typically comprises material having a basis weight greater than that of hosiery and less than conventional undergarments in order to provide a desired "sheerness".

As shown in FIGS. 1 and 2, the front region 30 is that portion of diaper 20 that cooperates with the rear region 40 to encircle a wearer's waist and hips. The front region cooperates with the rear region to define a waist opening 21 that allows entry into the diaper, and to provide an adjustable waistband such that the waist opening conforms to a wearer's waist. The adjustable waistband may be an adjustable belt, but typically is an elasticized waistband, such as elasticized waistband 22. The elasticized waistband may be formed by providing an elastic member, such as Lycra® or spandex material, adjacent each distal end of the blank shown in FIG. 3. The elasticized waistband typically comprises the same yarn as, and is integrally knit with, the front region and the rear region. More typically, the elasticized waistband comprises a turned welt as known in the art. One knitting pattern for the elasticized waistband comprises a combination of plain knit stitches and float stitches wherein every fourth wale is provided with a positive float stitch. The front, rear, and crotch regions also cooperate to define the leg openings 60, as shown in FIG. 1.

The front region 30 can be cut to an appropriate shape from a woven or nonwoven material and joined to the remaining portions of the diaper 20, but is typically wholly plain knit, more typically jersey knit, from a combination of elastically extensible and non-elastically extensible yarns. The elastic properties of the individual yarns and the particular knitting pattern can be used to define the mechanical properties of the front region. In one embodiment, the front region comprises wholly plain knit, e.g., jersey knit, using Lycra® or spandex yarn having suitable mechanical properties in all courses. Other knitting patterns and alternative yarns can be used to provide the desired mechanical properties.

While the front region 30 need not comprise elastic material, it is typically extensible in both the longitudinal and lateral directions. Such elastic extensibility enables the diaper 20 to fit a variety of bodily shapes and sizes and provides good conformity to a wearer's body. An extensible front region further cooperates with the rear region 40 and the crotch region 50 to provide an upward holding force within the crotch region of the diaper throughout a wide range of wearer movements. The upward holding force helps maintain an article, such as absorbent pad 200 shown in FIG. 4, worn with the diaper in close bodily contact in the wearer's crotch region. The upward force directs the absorbent pad 200 such that it is held closely against the wearer's body, wherein the front edge 202 of the pad lies in a position anterior to the genitalia and the rear edge 204 typically lies posterior to the anus. The upward force also helps maintain the absorbent pad in position throughout a wide range of wearer motions.

The crotch region 50 is positioned along the longitudinal centerline L of diaper 20 between the front region 30 and the rear region 40. The crotch region cooperates with the front region and the rear region to define the leg openings 60. The crotch region is that portion of the diaper that supports the absorbent article, such as absorbent pad 200, and holds it in close bodily contact in the wearer's crotch area. The crotch region has a generally trapezoid shape. When measured in a flat and non-extended state, the crotch region for an adult typically has a width measured 10.0 cm above the lateral centerline of from about 6.0 to about 15.0 cm, and a width at the lateral centerline of from about 1.5 to about 10.0 cm. Typically, the crotch region has a width measured 10.0 cm above the lateral centerline of from about 8.0 to about 12.0 cm, and a width at the lateral centerline of from about 2.5 to about 8.0 cm. In one embodiment, the crotch region has a width measured 10.0 cm above the lateral centerline of from about 9.0 to about 11.0 cm, and a width at the lateral centerline of from about 4.0 to about 5.0 cm. When used with an absorbent article in a system of the invention, the crotch region width typically is greater than or equal to the width of the primary absorbent core.

The crotch region 50 cooperates with the front region 30 and the rear region 40 so that the diaper 20 as worn provides a comfortable but sufficient upward holding force against the article. Without being bound by theory, it is believed that the upward holding force provided by the crotch region against the article is due at least in part to the compressive holding force provided by the stretch material therein. When the crotch region is stretched in use, the material exerts compressive forces against the article so as to hold it closely against the wearer's crotch area. This conformity is maintained over a wide range of body movement, e.g., close pad-to-body contact is maintained when a wearer's legs are close together, spread apart, and/or moving front to back during walking. The holding force is great enough to securely hold the article against the body, but not great enough to cause wearer discomfort or to push the article out of position, especially during body movement. The crotch material typically has relatively low stretch modulus and provides relatively high "available stretch" as worn. This high available stretch in both the lateral and longitudinal directions, combined with sufficient but relatively low holding force, helps to maintain the article in close bodily contact across a range of body sizes, article (e.g., pad) sizes, and body motions. The crotch region of the diaper has a Crotch Holding Force (CHF-4.0) of greater than about 0.1 kgf, typically greater than about 0.2 kgf, as measured by the Crotch Holding Force method presented herein. In one embodiment, the crotch region has a Crotch Holding Force (CHF-5.5) of greater than about 0.2 kgf, typically greater than about 0.3 kgf. The crotch region also has a Crotch Holding Force (CHF-2.0) of less than about 1.0 kgf, typically less than about 0.8 kgf, more typically less than about 0.6 kgf. In one embodiment, the crotch region has a Crotch Holding Force (CHF-4.0) of less than about 1.0 kgf, typically less than about 0.8 kgf, more typically less than about 0.6 kgf. In another embodiment, the crotch region has a Crotch Holding Force (CHF-5.5) of less than about 1.0 kgf, typically less than about 0.8 kgf. In yet another embodiment, the crotch region has a Crotch Holding Force (CHF-6.5) of less than about 1.4 kgf, typically less than about 1.2 kgf.

The crotch region 50 can comprise any woven material, nonwoven material (with stretch incorporated as known in the art), knit material, or the like that possesses the requisite physical properties. Similarly, the crotch region can comprise one material or a combination of materials, stitching, and/or design patterns that collectively possess the requisite physical properties. The crotch region can be cut to an appropriate shape and size, and joined to the remaining portions of the diaper. The crotch region is typically wholly plain knit, more typically jersey knit, from a combination of elastically extensible and non-elastically extensible yarns. The elastic properties of the individual yarns and the particular knitting pattern can be used to define the mechanical properties of the crotch region. In one embodiment, the crotch region comprises wholly plain knit, e.g., jersey knit, using elastomeric fiber material such as Lycra® or spandex yarn having suitable mechanical properties in all courses. Other knitting patterns and alternative yarns can be used to provide the desired mechanical properties. Typically the crotch region comprises a knit material having a Crotch Holding Force similar to that of the material used to construct the front region 30 and/or the rear region 40. More typically, the crotch region is integrally knit with the front region and/or the rear region using a plain knit pattern. Suitable yarns include natural yarns, such as cotton yarns and wool yarns, and synthetic yarns, such as nylon yarns, polyester yarns, acrylic yarns, and combinations thereof, e.g., nylon yarns and cotton yarns. Typically, elastomeric fiber material such as Lycra® or spandex yarns are used with these natural and/or synthetic fibers to provide the desired stretch properties. In one embodiment, the crotch region of the diaper comprises from about 5% to about 30%, typically from about 10% to about 25%, more typically from about 15% to about 20%, of the elastomeric fiber material, e.g., Lycra®. For example, the crotch region of the diaper may comprise from about 80% to about 85% nylon yarn and from about 15% to about 20% of Lycra®.

The rear region 40 cooperates with the front region 30 to encircle a wearer's waist and hips. The rear region can be pre-attached to the front region providing a pull-up type diaper configuration. Alternately, at least two fastening systems can be attached to the rear region that when assembled, cooperates with the front region to provide an adjustable waistband and encircle a wearer's waist and hips. This configuration provides an hour-glass type diaper design. As shown in FIG. 2, the rear region in the diaper may cover a wearer's buttock.

As described above regarding the front region 30, the rear region 40 may comprise a woven or nonwoven material, but typically comprises wholly plain knit, e.g., jersey knit, from a combination of elastically extensible and non-elastically extensible yarns. The elastic properties of the individual yarns and the particular knitting pattern can be chosen to define suitable mechanical properties. In one embodiment, the rear region comprises wholly plain knit, such as jersey knit, using Lycra® or spandex yarn having suitable mechanical properties in all courses. Other knitting patterns and alternative yarns can be used to provide the desired mechanical properties.

While the rear region 40 need not comprise an elastic material, it is typically extensible in both the longitudinal and lateral directions, particularly in portions of the rear region above the gluteal grove. Such elastic extensibility enables the diaper 20 to fit a variety of bodily shapes and sizes and provides good conformity to a wearer's body. The extensible rear region further cooperates with the front and crotch regions to provide an upward holding force within the crotch region throughout a range of wearer movements. Such an upward force helps maintain an article (such as absorbent pad 200 shown in FIG. 4) worn with the diaper in close bodily contact in the wearer's crotch region. The rear region typically comprises material having a Crotch Holding Force in the range described above for the crotch region. The front, crotch, and rear regions are often comprised of the same material.

The front, crotch, and/or rear regions of the diaper may comprise at least one additional extension or panel extending beyond these regions so long as it does not significantly interfere with the function of the diaper. For example, the rear region may comprise one or more additional extensions or panels extending partially or fully over the buttocks that do not significantly interfere with the function of the diaper. FIG. 3 illustrates the addition of an extension 66 to the front, crotch and rear regions of the diaper 20. (The extension 66 is shown on only one side of diaper 20, but when present it typically would be on both sides of the diaper.) If such extensions are added, additional side elastics such as elastics 62 may be attached to the periphery of the extensions, or the side elastics may be omitted.

As can be seen in FIG. 1, the diaper 20 of the invention is provided with a pair of leg openings 60. The front region 30, the rear region 40, and the crotch region 50 cooperate to define the periphery of each leg opening 60. This periphery typically is provided with side elastic 62 for elasticization of the leg opening. The side elastics 62 provide contractive forces around the periphery of the leg opening 60 contributing to the fit of the diaper. The contractive forces should be great enough to fit comfortably against the body and help hold the article, and particularly any wings on the article, in contact with the body through the range of body motions. The contractive forces should not be so great as to cause discomfort to a wearer or adversely affect the holding properties of the crotch region. Typically, the side elastics have a relatively low stretch modulus and provide relatively high available stretch as worn. Such side elastics cooperate with the crotch region to provide a sufficient, comfortable and relatively uniform upward holding force against an article to hold it closely against a wearer's crotch area.

The side elastics 62 may be joined to the front region 30, the rear region 40, and the crotch region 50 about the periphery of the leg opening 60 using methods known in the art, e.g., using adhesive means or by mechanical means, such as stitching. The side elastics may be joined to portions of the side edges 25, 26, 27 and 28 surrounding the leg openings (i.e., that form the periphery thereof). Alternately, the side elastics may be integrally formed, for example, formed during the knitting process, using methods known in the art. For a knit diaper, the side elastics are typically joined to the front region, the rear region and the crotch region by stitching.

The crotch region 50 of the diaper 20 can also be provided with indicia, e.g., "placement guides" or "position guides", to help a wearer optimally position a compatible or coordinated article therein. Such indicia can comprise markings along the longitudinal centerline L of the diaper to help a wearer reliably position the article on the inner surface of the crotch region. Placement guides 64 shown in FIGS. 1 and 3 are examples of such indicia. Alternatively, the indicia can comprise markings on the side elastics 62 in the crotch region of the diaper to help a wearer properly position wings on the article.

It will be appreciated that the diaper herein may have other configurations besides those shown and described. For example, the front region may comprise one or more additional straps, strings, panels, or cut-out areas between the crotch region and the adjustable waistband. Other styles, designs, and configurations, such as "bikini", "thong", etc., that comprise the front, crotch, and rear regions herein are within the scope of the present invention. As described above, the diaper may comprise at least one extension or panel extending beyond the front, crotch, and/or rear regions so long as it does not significantly interfere with the function of the diaper.

The diaper of the invention can be made by various methods known in the art. Typically, a blank for the diaper is first knit in a tubular form using means known to the art. For example, the front region 30, the rear region 40, and the crotch region 50 of diaper 20 can be integrally knit. Appropriate knit patterns as described above can be used. In one embodiment, portions of the tubular knit blank are cut out to provide the leg openings 60 of diaper 20. For example, a tubular blank can be flattened such that the interior faces thereof contact each other and a pair of longitudinally oriented side edges are formed. Leg opening precursors can then be formed by cutting matching portions having a semi-circular, semi-elliptical, or other desired shape from transversely opposite side edges at regular intervals along the flattened blank. Diaper blanks are then formed by transversely cutting the flattened tubular blank in a predetermined repeat pattern wherein a first transverse cut is made across the material not removed when the leg opening precursors are formed to create a crotch portion precursor, and a second transverse cut is made across the full width of the flattened tubular blank forming the waist opening 21. The leg elastics 62 are disposed about the periphery of each leg opening and joined thereto. The two ends formed by the first transverse cut are joined by a single transverse seam to complete the crotch region 50. The diaper 20 is then finished by forming a turned welt elasticized waistband about the periphery of the waist opening.

Alternatively, a tubular blank for the diaper 20 can be slit walewise and opened. Excess material that would otherwise fill the leg openings 60 is removed to form a flat blank for the diaper having a front end edge 23, a rear end edge 24, front side edges 25 and 26, and rear side edges 27 and 28. The side elastics 62 are joined to the diaper about the periphery of the leg openings as discussed above. The blank for the diaper is then folded about the lateral centerline T, and opposing portions of the side edges that lie between the leg opening and the end edges 23 and 24 are joined (e.g., by sewing the edges) to form seams at sides 32 and 34 completing the assembly of the diaper. In one embodiment, the portion of side edge 25 that lies between the end of the side elastic 62 in the front region and the end edge 23 is joined to the portion of side edge 27 that lies between the end of the side elastic in the rear region and the end edge 24 to form a seam at side 32. Side edge 26 is joined to side edge 28 in a similar manner to form a seam at side 34.

Figure 17:
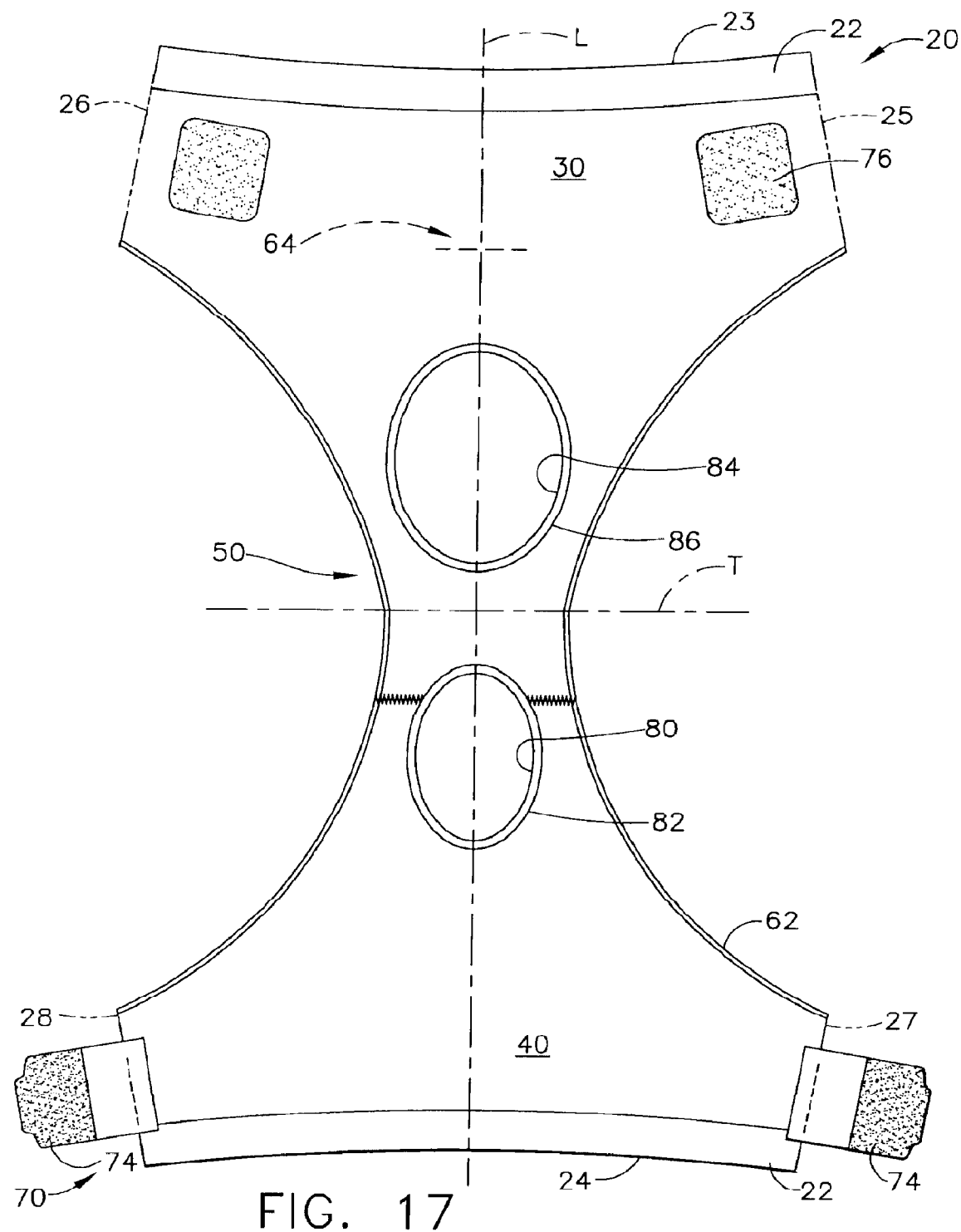
FIG. 17 is a plan view of a diaper of the invention comprising first and second openings.
Figure 19:
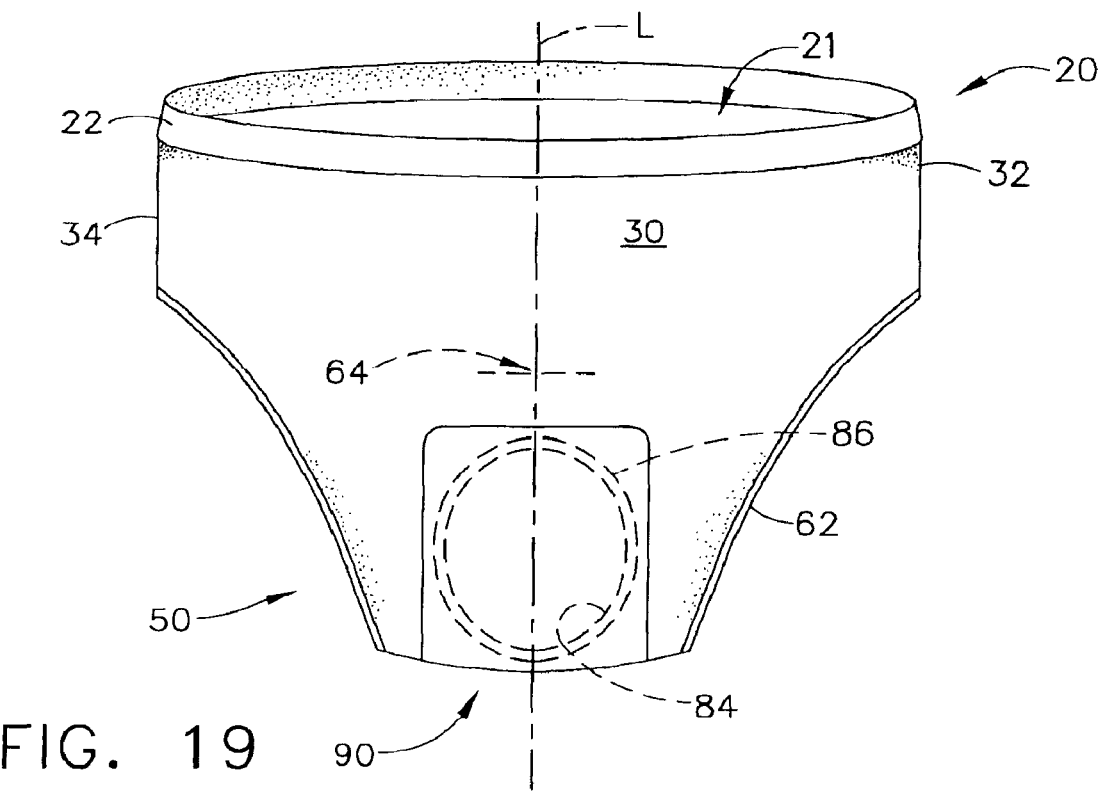
FIG. 19 is a front view of a diaper of FIG. 18 with an absorbent article covering the opening.

In another embodiment shown in FIG. 17, an hour-glass type diaper of the invention comprises a crotch region 50 having a first opening 80 located at the anus of an individual when the article is worn and a second opening 84 located at the urethral opening when the article is worn. In the embodiment shown, first opening 80 comprises elastics 82 around the periphery of the opening. Second opening 84 comprises elastics 86 around the periphery of the opening. In another embodiment shown in FIG. 18, a pull-on type diaper of the invention comprises a crotch region 50 having a first opening 80 located at the anus of an individual when the article is worn and a second opening 84 located at the urethral opening when the article is worn. Both openings 80 and 84 comprise elastics around the periphery of the openings. FIG. 19 shows an absorbent article 90 covering the opening 84 for receiving urine. Similarly, an first absorbent article may cover another opening for receiving feces. In one embodiment, the diaper comprises a first fastening material and each absorbent article comprises a second fastening material that cooperatively engage the first fastening material and enables each absorbent article to be removably affixed to the diaper. Typically, the first and second fastening materials comprise mechanical fastening material, but in other embodiments, adhesive material may be used to removably hold the article to the diaper. In another embodiment, the diaper may comprise at least one flap or pocket for receiving and supporting the first or second absorbent article.

The diaper of the present invention can be used with a wide variety of compatible articles, particularly absorbent articles, including pads, diaper inserts, sanitary pads, incontinence pads, BM pads, fluid collection bags, urine collection bags, feces collection bags (i.e., BM collection bags), and other absorbent articles capable of being held in close bodily contact in the crotch region of the wearer. Such an article has a compatible shape and size, and may fit within the low-motion zone of the wearer thereby avoiding significant leg movement interactions that can interfere with close bodily contact in the crotch region. The invention thus provides a system comprising the diaper herein and a compatible article for use therewith. While not intending to be limited by theory, it is believed that the article/diaper system provides improved performance because the diaper maintains the article (e.g., a pad) in close bodily contact in the crotch region of the wearer, both the article and the diaper may fit within the low-motion zone of the body, and/or the article and diaper are designed to work together in a coordinated manner.

Figure 4:
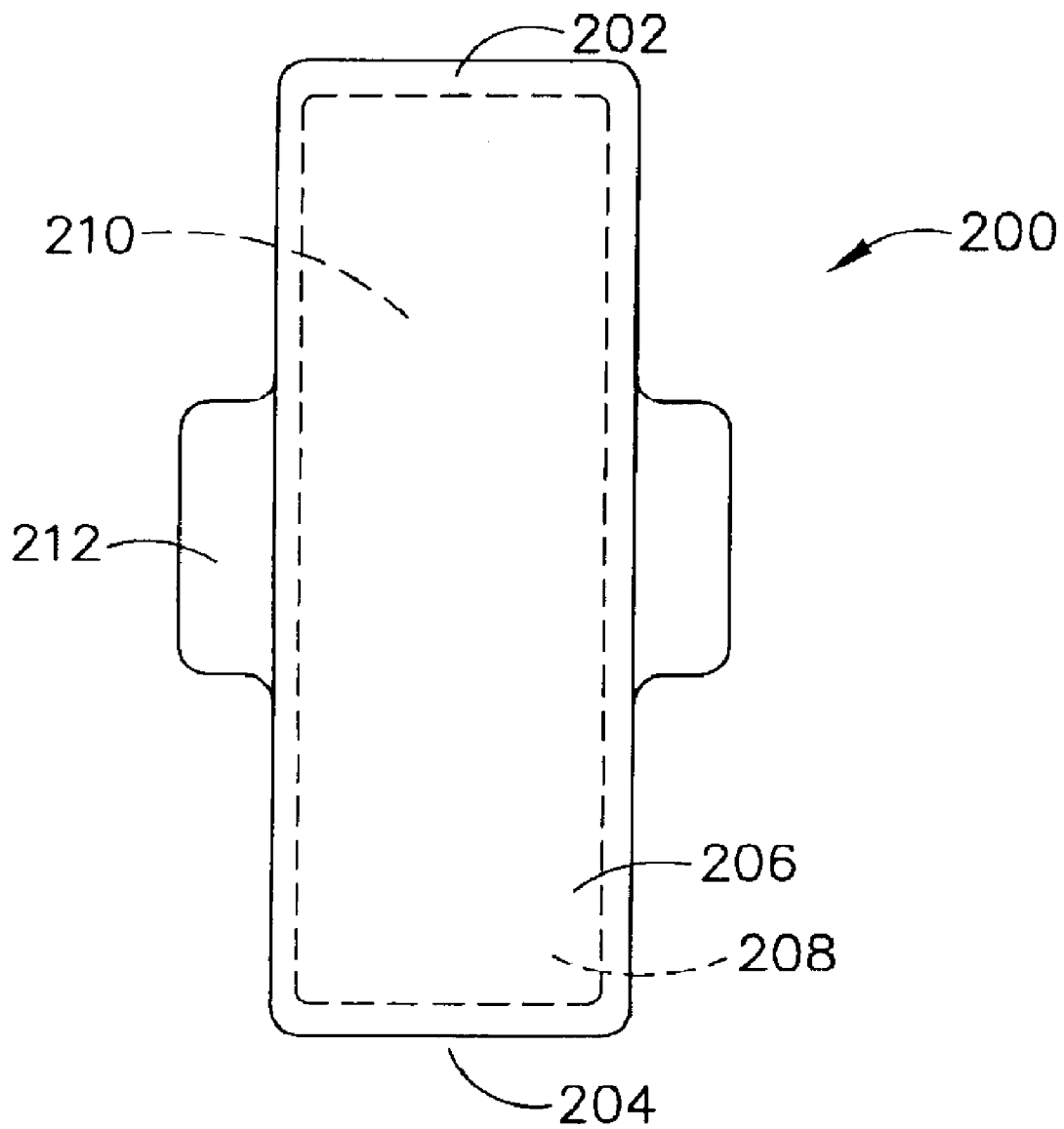
FIG. 4 is a plan view of an absorbent pad suitable for use with a diaper of the invention.

FIG. 4 is a plan view of one such compatible absorbent article suitable for use in the system of the present invention. In this embodiment, the absorbent article is a pad designated 200. In one embodiment, the absorbent article has an absorbent capacity of at least about 50 grams of fluid, typically at least about 100 grams of fluid, and more typically at least about 200 grams of fluid. In another embodiment, the article has a caliper of greater than about 5.0 mm, typically greater than about 7.0 mm, and more typically greater than about 10.0 mm. Other compatible absorbent articles for use herein are described in U.S. Pat. No. 6,393,621, Redwine et al.; U.S. Pat. No. 6,582,411, Carstens, et al.; PCT Application WO 99/25289; U.S. Pat. No. 5,354,400, Lavash, et al.; and U.S. Pat. Nos. 4,687,478 and 5,267,992, Van Tilburg; all incorporated herein by reference.

In other embodiments, the absorbent articles may be designed to absorb only urine, or only BM, or both. In such cases, one or more absorbent articles may be used with the diapers of the invention.

An article herein has at least two surfaces, a liquid pervious side, i.e., a body-contacting surface or "body surface", and a liquid impervious side, i.e., a diaper-contacting surface, opposite the liquid pervious side. The body surface is worn adjacent to the wearer's body. The diaper surface is placed adjacent to the supporting diaper when the absorbent article is worn. An absorbent article typically also comprises an absorbent component, such as an absorbent core, between the liquid pervious side and the liquid impervious side. The liquid pervious and impervious sides are arranged to form a unitary structure, with the absorbent component therebetween. An absorbent article herein will be described in detail with reference to the absorbent pad 200 shown in FIG. 4.

The absorbent pad 200 has two centerlines, a longitudinal centerline and a lateral centerline. The term "longitudinal" refers to a line, axis or direction in the plane of the pad that is generally aligned with (e. g., approximately parallel to) a vertical plane that bisects a standing wearer into left and right body halves when the pad is worn. The term "lateral" refers to a line, axis or direction that lies within the plane of the pad that is generally perpendicular to the longitudinal direction.

The absorbent pad 200 has two spaced apart side edges, and two spaced apart end edges (or "ends"), which together form the periphery of the article. When worn, the front edge 202 of the pad typically lies in a position anterior to the genitalia and the rear edge 204 lies posterior to the anus. In the embodiment shown in FIG. 4, the pad has a generally flat configurations. However, other suitable configurations, including cup-shaped configurations such as disclosed in U.S. Pat. No. 6,582,411, may be used.

The article and any absorbent core may have any suitable plan view configurations, including, but are not limited to: oval; race-track shaped; and shapes that have convexly-inward longitudinal side edges (e.g., hourglass shapes).

An absorbent article typically has an absorbent capacity of at least about 100 grams of fluid. Other absorbent articles for use herein may have more or less absorbent capacity. Such articles can be designed to meet different absorbency needs ranging from a light incontinence pad having an absorbent capacity of less than about 50 grams of fluid to an heavy incontinence pad having a capacity of more than about 200 grams of fluid.

The absorbent article typically comprises at least three primary components: a liquid pervious topsheet, a liquid impervious backsheet, and an absorbent component such as an absorbent core positioned between the topsheet and the backsheet. The liquid pervious topsheet, the liquid impervious backsheet, and the absorbent component can comprise a number of suitable materials provided that the absorbent article has the overall characteristics described herein.

It should be understood that articles herein are not limited to structures that have these three primary components. Articles can be provided that only have one or two of these components, or have additional components. For example, an absorbent article need not have a topsheet if the body-contacting surface of the absorbent core is suitable for use as a topsheet. A liquid impervious component, such as a liquid impervious backsheet, could be joined to the other side of the absorbent component. Alternatively, an absorbent article can comprise an absorbent component that has a liquid pervious side and a liquid impervious side. The liquid impervious side can be provided by treating the diaper-contacting surface of the absorbent component to render it liquid impervious.

While the articles described herein and any component topsheet, absorbent core and backsheet materials are typically disposable, they may be designed to be cleaned, laundered, restored, and/or reused after use. The article may thus comprise washable, reusable material.

Diaper absorbent pads are often worn in loose-fitting diapers. Such pads are typically designed to be large enough so that in the event of any shifting of the pad from its position under the genitalia and/or anus, it will still be able to intercept the wearer's bodily discharges. If an absorbent article with sufficient absorbent capacity is held closely against the wearer's crotch region, and in particular covers the genitalia and/or anus, the article can be of a reduced size. Such an absorbent article need only be large enough to cover these regions of the wearer's body, rather than being sized to accommodate shifting of the article. The absorbent article and diaper herein typically function by capturing body fluids at or near their source, using comfortable forces to hold the article in place at the source of the body exudates.

The liquid pervious side of the article herein is the body-contacting surface of the article. The liquid pervious side typically comprises a standard nonwoven web. Suitable fibers useful for making such a nonwoven web include polyolefin and polyester fibers. The nonwoven web typically has a basis weight from about 20 to about 200 grams per square meter, e.g., from about 30 to about 100 grams per square meter.

In some embodiments, the liquid pervious side comprises a plurality of elements extending outward from the body-contacting surface of the absorbent article. If the body-contacting surface is considered to lie within the X-Y plane, these elements will extend outward from this plane in the Z-direction. These elements can form any suitable angle with the body-contacting surface of the absorbent article. The elements can comprise any suitable type of components, including, but not limited to, fibers.

In one embodiment, the liquid pervious topsheet comprises a high loft fibrous material. The term "high loft fibrous material" refers to a low density, but relatively high caliper, fibrous material. The high loft fibrous material typically has a density of less than or equal to about 0.01 g/cm$^3$, and a caliper of greater than or equal to about 3.2 mm, typically between about 6.4 mm and about 13 mm. The high loft fibrous material typically has a basis weight of less than or equal to about 142 grams/m$^2$. The calipers and densities for such material are measured under INDA standard test method IST 720.1-92, which specifies measuring caliper under a pressure of 350 Pa.

The high loft fibrous material often comprises of fine polymeric fibers, which typically have a denier per fiber of less than or equal to about 6. The high loft fibrous topsheet material serves several functions. It allows the article to achieve a "macro" fit that is capable of fitting virtually all wearers, and a "micro" fit that adjusts to the particular body contours (which may be in the form of rugosities) of individual wearers. Another advantage of the high loft topsheet is that it is very soft and "cushiony". The high loft topsheet also is advantageous because it has a low coefficient of friction against the wearer's body due to the discrete contact of the individual fibers with the wearer's body.

In some embodiments, the high loft topsheet comprises a thermally bonded polyester fibrous nonwoven material having a caliper of about 4 mm and a basis weight of about 50 grams/m$^2$. The fibers of this high loft topsheet material are typically in a random orientation. One particular material for the high loft topsheet has a caliper of 4.1 mm and a density of 0.0077 g/cm$^3$. Another high loft topsheet material has a caliper of 5.8 mm and a density of 0.0098 g/cm$^3$ (after rebulking). If the high loft topsheet material has one side that is relatively flat and one side that is "fluffy", the flat side is typically oriented toward the absorbent core of the article.

In other embodiments, the liquid pervious topsheet may comprise an apertured film, such as an apertured, formed film. Suitable formed films are described in U.S. Pat. No. 3,929,135, Thompson; U.S. Pat. No. 4,324,245, Mullane, et al.; U.S. Pat. No. 4,342,314, Radel, et al.; U.S. Pat. No. 4,463,045, Ahr, et al.; and U.S. Pat. No. 5,006,394, Baird; all incorporated herein by reference.

The absorbent core may be manufactured in a wide variety of sizes and shapes (e. g., rectangular, thong-shaped, oval, hourglass, dog bone, asymmetric, etc.), and from a wide variety of absorbent materials commonly used in absorbent pads and other absorbent articles. The absorbent core, however, should typically be adapted so that it has the capacity specified herein. Examples of suitable absorbent materials include comminuted wood pulp, generally referred to as airfelt; creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; cotton cloth; or any similar material or combinations of materials, or mixtures thereof The configurations and construction of the absorbent core may also be varied. For example, the absorbent core may have varying caliper zones, e.g., it may be profiled to be thicker in the center, or may comprise hydrophilic gradients, superabsorbent gradients, or lower density and lower average basis weight acquisition zones, or it may comprise one or more layers or structures.

The backsheet of the absorbent article herein can be any suitable flexible, liquid impervious material. Typically, the backsheet is a polyethylene film having a thickness of from about 0.013 mm to about 0.05 mm. Suitable polyethylene films are manufactured by Clopay Corporation under the designation P18-0401 and microflex 1401. The backsheet may be embossed and/or matte finished to provide a more cloth like appearance. Further, the backsheet may permit vapors to escape from the absorbent core (i.e., it may be breathable) while still preventing exudates from passing through the backsheet. A suitable breathable backsheet material comprises an adhesively attached laminate of an apertured film having tapered capillaries, such as that described in U.S. Pat. No. 3,929,135, Thompson, and a microporous film. A suitable microporous film is supplied by Exxon Chemical USA, and described in U.S. Pat. No. 4,777,073, Sheth. The breathable backsheet is typically arranged so that the smaller openings of the tapered capillaries face the absorbent core. The microporous film is joined to the side of the apertured film having the larger openings to form the diaper-contacting surface of the absorbent article. In one embodiment, both the absorbent article and the crotch region of the diaper are vapor permeable.

Absorbent pads and other absorbent articles herein often comprise wings or flaps that extend laterally from a central absorbent component and are folded around the edges of the diaper in the crotch region. The wings typically are provided with an attachment means (e.g., adhesive) for affixing the wings to the outside of the diaper in the crotch region. The wings cover the sides of the diaper and minimize or prevent exudate soiling of the diaper in these covered areas. Typically, longer wings provide better side soiling protection. The wings may also help stabilize and hold the article and prevent it from shifting out of place, especially when the wings are affixed to the outside of the diaper. Therefore, longer wings are also desirable to improve the stability and "stay-in-place" performance of the article. The stability of longer wings, combined with increased side coverage, further improves the soiling protection provided by the system of this invention. In one embodiment, the article comprises wings having a length at least about 75%, typically at least about 80%, and more typically at least about 85% (e.g., at least about 90%) of the length of the absorbent article. Alternately, the absorbent articles could also comprise wings that could be removably attached to the body side of diaper 20 of this invention through openings 80 and 84 of FIG. 17. Wings used in this manner may also help stabilize and hold the article and prevent it from shifting out of place. Suitable wings are described in U.S. Pat. Nos. 4,687,478 and 5,267,992, Van Tilburg, and in U.S. Pat. No. 5,354,400, Lavash, et al., all incorporated herein by reference.

In another embodiment, the absorbent article comprises such long wings and a primary absorbent core having a width less than or equal to the width of the crotch region of the diaper. As used herein, the width of the absorbent core relative to the width of the crotch region of the diaper is measured when the article is placed in the diaper as it is intended to be worn. In one embodiment, the primary absorbent core has a width at least about 5.0 mm less than the width of the crotch region of the diaper along at least a portion of the article's length, typically along a majority of the absorbent article's length, and more typically along substantially all of the absorbent article's length. The primary absorbent core typically has a width at least about 10.0 mm less, and more typically at least about 15.0 mm less (e.g., at least about 20.0 mm less), than the width of the crotch region of the diaper along at least a portion of the absorbent article's length, typically along a majority of the absorbent article's length, and more typically along substantially all of the absorbent article's length. The combination of long wings and such a wider crotch region than the primary absorbent core often provides a barrier leg cuff configurations that improves containment of body exudates by the side elastics in the crotch region of the diaper. In embodiments having thicker absorbent cores, more narrow absorbent cores and/or wider diaper crotch regions can be selected to improve containment by such barrier leg cuff configurations.

The topsheet, the backsheet, and the absorbent core may be assembled in a variety of configurations known in the art, including layered or "sandwich" configurations and wrapped or "tube" configurations. In one embodiment, the absorbent pad 200 is assembled in a sandwich construction in which the topsheet and the backsheet have length and width dimensions generally larger than those of the absorbent core. The topsheet and the backsheet extend beyond the edges of the absorbent core to form portions of the periphery.

The topsheet may be joined to the body-contacting side of the absorbent core. In other embodiments, the topsheet need not be joined to the absorbent core to enhance the flexibility of the pad. The term "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The backsheet need not be, and typically is not, joined to the absorbent core to enhance the flexibility of the absorbent article. The portions of the topsheet and backsheet that extend beyond the edges of the absorbent core to form the periphery are typically joined to each other. If the topsheet is joined to the absorbent core, it can be joined to the core in any suitable manner known in the art. The topsheet may be joined to the core by a uniform continuous layer of adhesive, a patterned layer of adhesive, or an array of separate lines, spirals, or spots of adhesive.

At least the liquid pervious side and the liquid impervious side of the absorbent article are arranged to form a "unitary structure." The term "unitary structure" refers to a construction in which the components are joined together, or integrated together as a unit. The term includes constructions such as those described above where the topsheet, absorbent core, and backsheet comprise separate components that are joined together. It also covers constructions in which the liquid pervious side and liquid impervious side of the absorbent article do not comprise a separate topsheet and/or backsheet. For example, in the latter case, the liquid pervious side, the liquid impervious side, or both, may comprise a surface of the absorbent core that has the desired characteristics, rather than a separate component.

FIGS. 5-19 show various absorbent articles suitable for use with diapers of the present invention. Absorbent pad 200 shown in FIG. 4 comprises front edge 202, rear edge 204, and adjoining side edges that together form the periphery of the pad. The pad also comprises a topsheet 206, a backsheet 208, and a primary absorbent core 210 that has a generally rectangular shape, with substantially straight side edges. The primary absorbent core comprises the significant absorbent material for fluid acquisition and storage, and typically is located directly beneath the genitalia and anus as worn. In one embodiment, the primary absorbent core 210 has a length of about 21.0 cm, a width near the front edge 202 and rear edge 204 of the pad of about 6.5 cm. The primary absorbent core also typically has a width that is less than the width of the crotch region of the diaper that will be used to hold the article. The pad thus has a size and shape compatible with the diaper so that it can be held in close bodily contact in the crotch region.

The pad 200 also comprises two side wings 212 that extend laterally from the central portion of the pad. The wings can be folded around the edges of the diaper in the crotch region to help stabilize the pad and prevent it from shifting out of place. The wings typically have a fastening system such as an adhesive or other attachment means to help secure them to the outer surface of the diaper in the crotch region.

Figure 5:
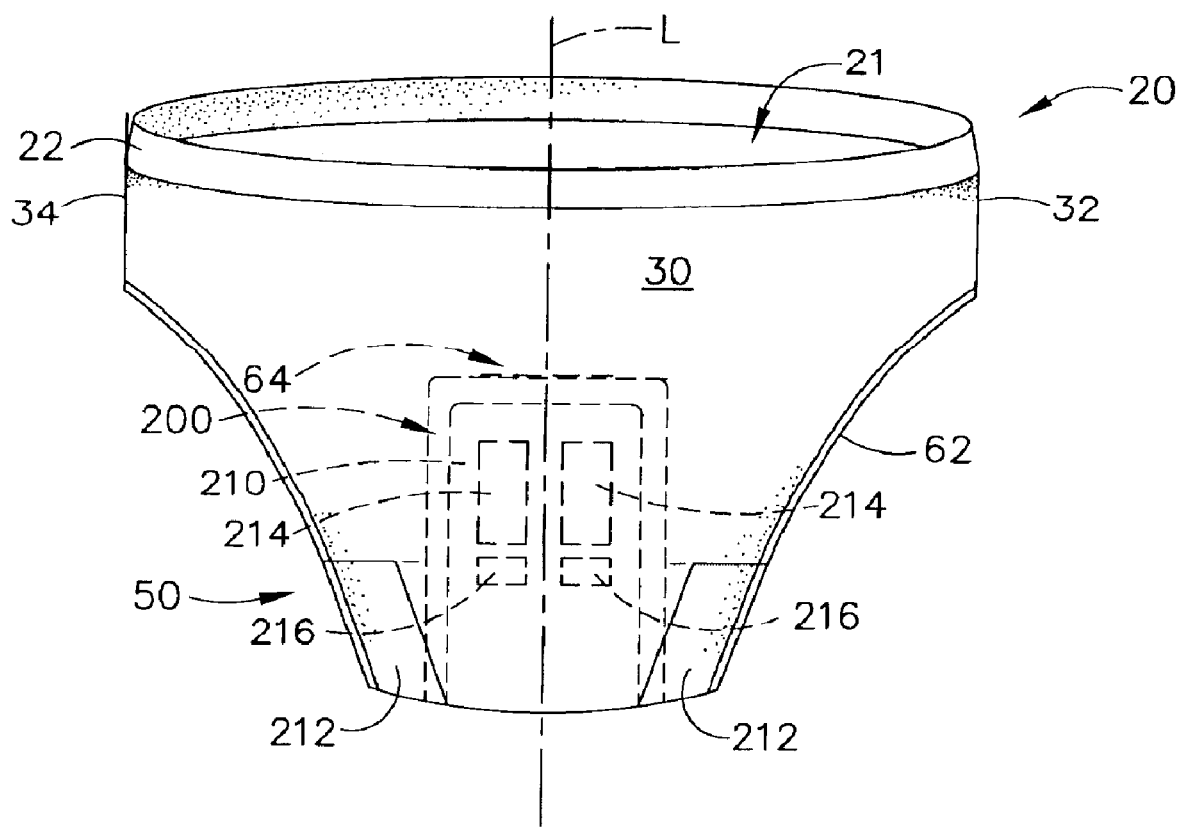
FIG. 5 is a front view of the pad of FIG. 4 further comprising fastening systems and worn with the diaper of FIG. 1.
Figure 7:
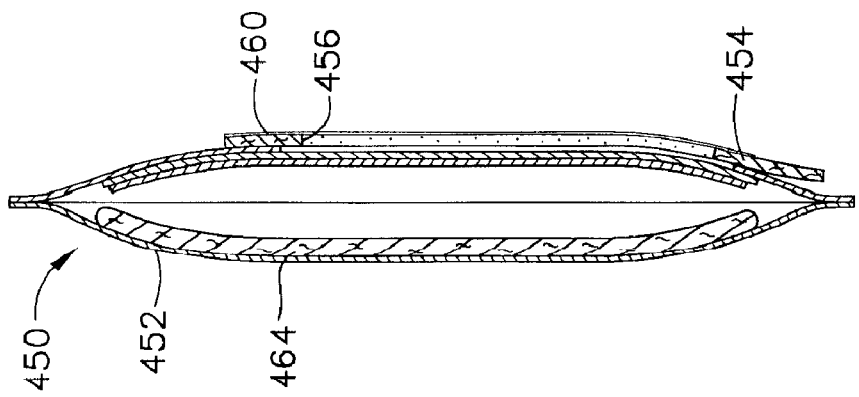
FIG. 7 is a sectional view of the device of FIG. 6 taken along line 7-7.
Figure 6:
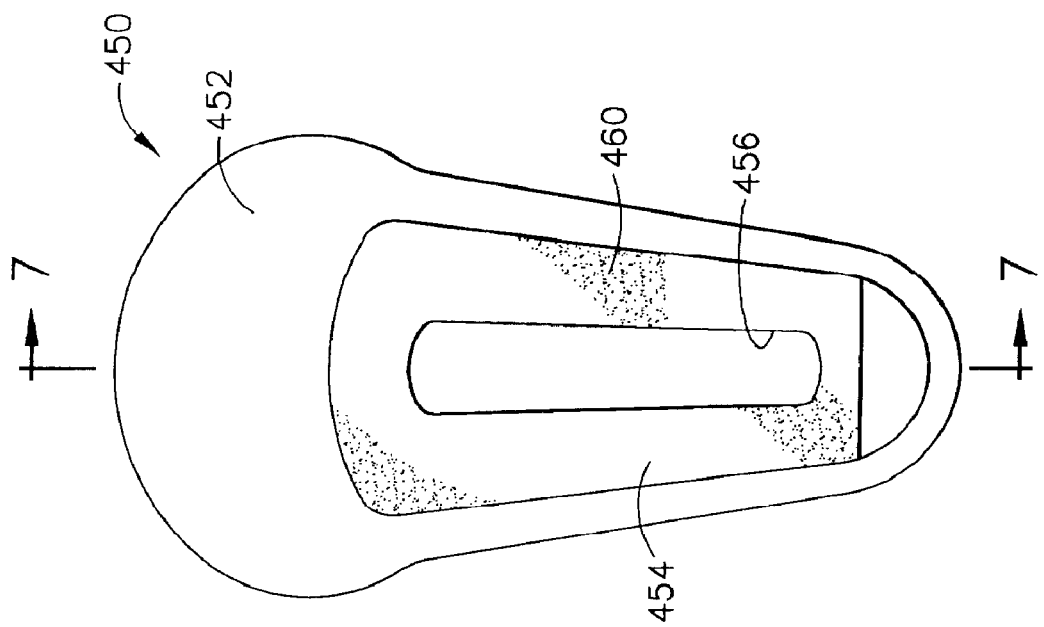
FIG. 6 is a plan view of an absorbent article fluid management device suitable for use with a diaper herein.

FIG. 5 is front view of the absorbent pad 200 of FIG. 4 further comprising fastening systems 214 and 216, and worn with the diaper 20 of FIG. 1. FIG. 5 thus illustrates one system of the present invention. In other embodiments, the absorbent articles may be designed to absorb only urine, or only BM, or both. In such cases, one or more absorbent articles may be used with the diapers of the invention. Other systems herein are obtained by combining the articles of FIGS. 4-15 and other articles described herein with the various diapers described herein. In the embodiment of FIG. 5, fastening system 214 is added to at least a portion of the liquid impervious side of the pad 200 to engage at least a portion of the body-contacting side of the crotch region of diaper 20. Fastening system 214 may comprise any suitable fastening material, including an adhesive material, a cohesive-adhesive material, a material having a high coefficient of friction, or a mechanical fastening material. The wings 212 of pad 200 are shown folded around the edges of the diaper in the crotch region and secured to the outer, garment-contacting side of the diaper. The wings also have a fastening system added to at least a portion of their liquid impervious side to engage at least a portion of the crotch region of diaper 20. The wing fastening system may also comprise any suitable fastening material, including an adhesive material, a cohesive-adhesive material, a material having a high coefficient of friction, or a mechanical fastening material. Although pad 200 in FIG. 5 comprises fastening systems 214 and 216, these are optional and one or both may be omitted. As can be seen, the pad has a size and shape compatible with the diaper so that it can be held in close bodily contact in the crotch region of the wearer. The primary absorbent core of the article typically is of a size and configurations to cover the wearer's crotch region and is capable of being held in close bodily contact by the diaper.

As described above, the diaper-contacting surface of the article typically comprises a fastening system for attaching the article to the diaper. The fastening system may comprise an adhesive material, including any of the pressure sensitive adhesives typically used to secure conventional sanitary pads to the crotch region of undergarments. Alternatively, the article/diaper system may comprise mechanical fastening material located on a portion of the liquid impervious side of the article that will engage with at least a portion of the crotch region of the diaper. The mechanical fastening material can be located on any suitable portion of the diaper-contacting surface of the article. The mechanical fastening material can be distributed in a pattern that matches the pattern of one or more pre-selected portions of the diaper. The alignment of the mechanical fastening material with portions of the diaper can be used as a placement guide to ensure that the absorbent article is positioned properly in the diaper. The pattern of mechanical fastening material can also be used to assist in fitting the absorbent article closely against the wearer's body. If the absorbent article comprises wings, at least a portion of the wings may comprise mechanical fastening material for engaging at least a portion of the crotch region of the diaper.

The absorbent pad 200 is typically utilized by placing it in the crotch region of the diaper 20, with one end extending toward the front region of the diaper and the other end towards the back region of the diaper. The backsheet of the pad is placed in contact with the inner surface of the center of the crotch region of the diaper. Fastening systems 214, shown in FIG. 5 on the diaper-contacting side of the absorbent pad, may comprise projections of mechanical fastening material for engaging with the knit material from which the crotch region of the diaper is typically made.

In one embodiment, the diaper-contacting surface of the absorbent article comprises a skin-friendly mechanical fastening material having a substrate or surface with an array of prongs in the form of a plurality of small hair-like projections disposed thereon, such as described in U.S. Pat. No. 6,582,411, Carstens, et al., incorporated herein by reference. Such projections are capable of easily adhering to knit material (e.g., the crotch region of the diaper), and have sufficient holding force even when the diaper stretches and contracts.

Cohesive-adhesive fastening systems, such as described in U.S. Pat. No. 5,415,650, Sigl, et al., incorporated herein by reference, are also suitable for use herein. The absorbent article is positioned on and held secure to the crotch region of the diaper by cohering a first cohesive-adhesive with the second cohesive-adhesive. For example, in FIG. 5, each of fastening systems 214 may comprise a) a first cohesive-adhesive at least partially impregnated or coated onto at least a portion of the liquid impervious side of the absorbent article, and b) a second cohesive-adhesive at least partially impregnated or coated on at least a portion of the crotch region of the diaper. As used herein, a "cohesive-adhesive" material is one that preferentially adheres to itself and not to other materials. If the absorbent article comprises wings, the liquid impervious side of each wing and an exterior surface of the crotch region of the diaper may be covered with a first and a second cohesive-adhesive, respectively, such that a first cohesive-adhesive present on the wings can cohere to a second cohesive-adhesive present on the exterior surface of the crotch region. The holding force provided by the crotch region combined with the fit within the low motion zone enhances the article stay-in-place performance of cohesive-adhesive fastening systems relative to that of conventional pad/pant systems.

The article/diaper system of this invention need not comprise any fastening adhesive or fastening material in order to hold the article in place. In one embodiment, the holding force provided by the crotch region of the diaper combined with the frictional forces between the article and the diaper are sufficient to hold the article in place. Similarly, an absorbent article with wings need not comprise an adhesive or other fastening material on the wings to help keep them in place.

Another fastening system for use herein is described in U.S. Pat. No. 6,613,175, Moscherosch et al., incorporated herein by reference. In one embodiment, the article has a low auto-adhesion attachment means for maintaining the article's position in use. The article is capable of being folded upon itself prior to use, and then unfolded without destroying any aspect thereof This eliminates the need for a separate release sheet to protect any positioning adhesive prior to use. This embodiment may reduce non-value-added costs, enhance consumer convenience by reducing the number of steps of use, and reduce environmental concerns by eliminating a portion of the product from the solid waste stream. The holding force provided by the crotch region of the diaper combined with the improved fit enhances the stay-in-place performance of such low auto-adhesive fastening systems.

Another fastening system for use herein is described in U.S. Pat. No. 6,595,977, Luizzi, et al., incorporated herein by reference. The article comprises a high coefficient of friction (COF) surface on the liquid impervious side (e.g., backsheet) of the article to help maintain its in-use position. The holding force provided by the crotch region of the diaper combined with frictional forces between such a high COF backsheet surface and the diaper are sufficient to hold the article in place. For example, in FIG. 5, each of fastening systems 214 may comprise a high COF surface on the backsheet 208 of the pad.

Another fastening system for use herein is described in U.S. Pat. No. 5,676,652, Hunter, et al., incorporated herein by reference. In one embodiment, the article has a pair of wings that are provided with mechanical fasteners. The wings extend laterally from a central absorbent component and are folded around the edges of the diaper to provide coverage and reduce soiling. The wings typically stay in place well enough to cover the side edges of the diaper without affixing them underneath the diaper. However, the wings may be provided with a skin-friendly mechanical fastening material for additional security.

Other absorbent articles useful herein are described in U.S. Pat. No. 6,761,710, D'Acchioli, et al., U.S. Pat. No. 6,551,292 D'Acchioli, et al., and U.S. Pat. No. 6,602,233 Palumbo, et al., incorporated herein by reference. In one embodiment shown in FIGS. 6 and 7, the absorbent article is a disposable fluid management device 450, such as a menstrual fluid or a urine fluid management device, comprising a bag 452 having a flange 454 and an aperture 456. The bag typically comprises an adhesive layer 460 having a first surface and a second surface opposed thereto, wherein first surface is disposed proximate to the aperture and on an external surface of the bag, and the second surface is capable of providing releasable attachment of the bag to the uro-genital area of a wearer. The aperture typically is surrounded by an adhesively faced flange for releasable attachment to the uro-genital area of the wearer. These disposable fluid management devices are designed to acquire, absorb, and contain various exudates discharged from the body, including urine and menses. The bags are typically liquid impermeable. An absorbent material 464 may be disposed within the bags. The absorbent material may be selected from the group consisting of comminuted wood pulp; creped cellulose wadding; meltblown polymers; chemically stiffened, modified or cross-linked cellulosic fibers; tissue; absorbent foams; absorbent sponges; superabsorbent polymers; absorbent gelling materials; and mixtures thereof The flange adhesive typically is selected from the group consisting of hydrogel adhesives, oilgel adhesives, hydrocolloid adhesives, and mixtures thereof.

Figure 9:
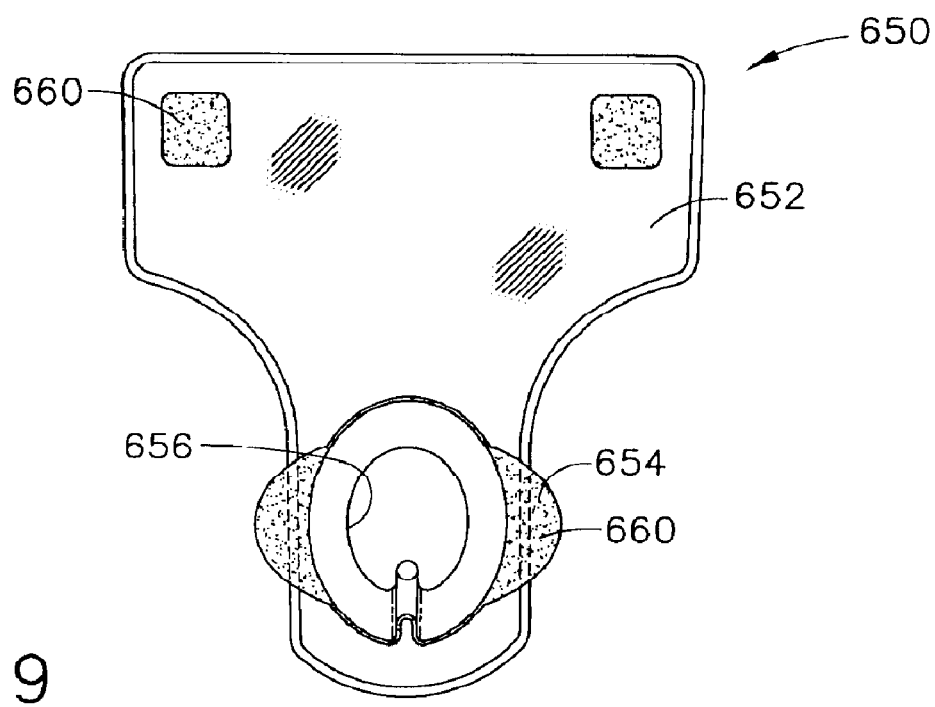
FIG. 9 is a plan view of an absorbent article urine management device suitable for use with a diaper herein.
Figure 10:
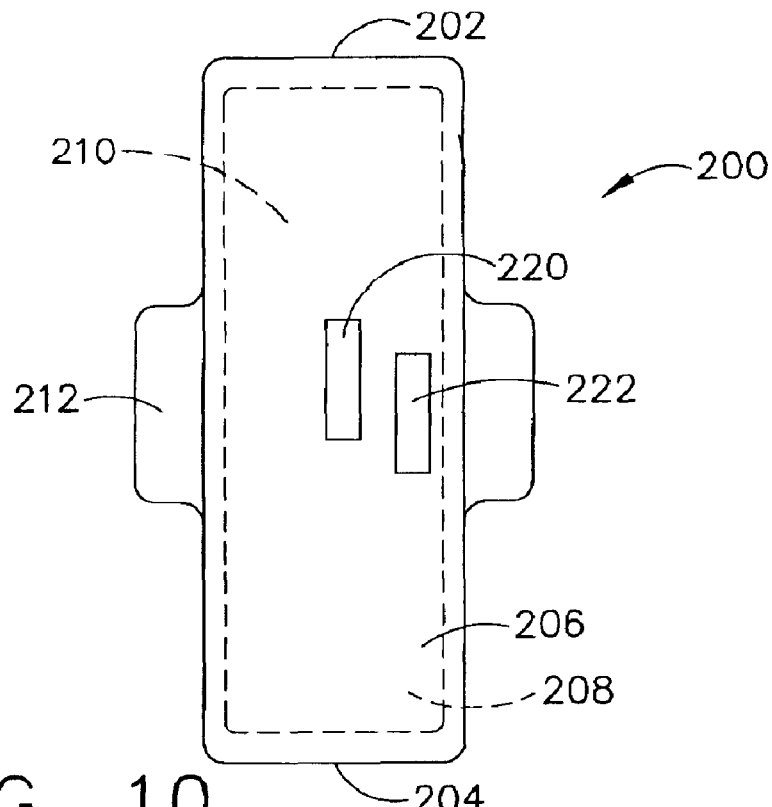
FIG. 10 is a plan view of the pad of FIG. 4 further comprising regions having compositions disposed thereon that are transferable to the wearer's skin.
Figure 11:
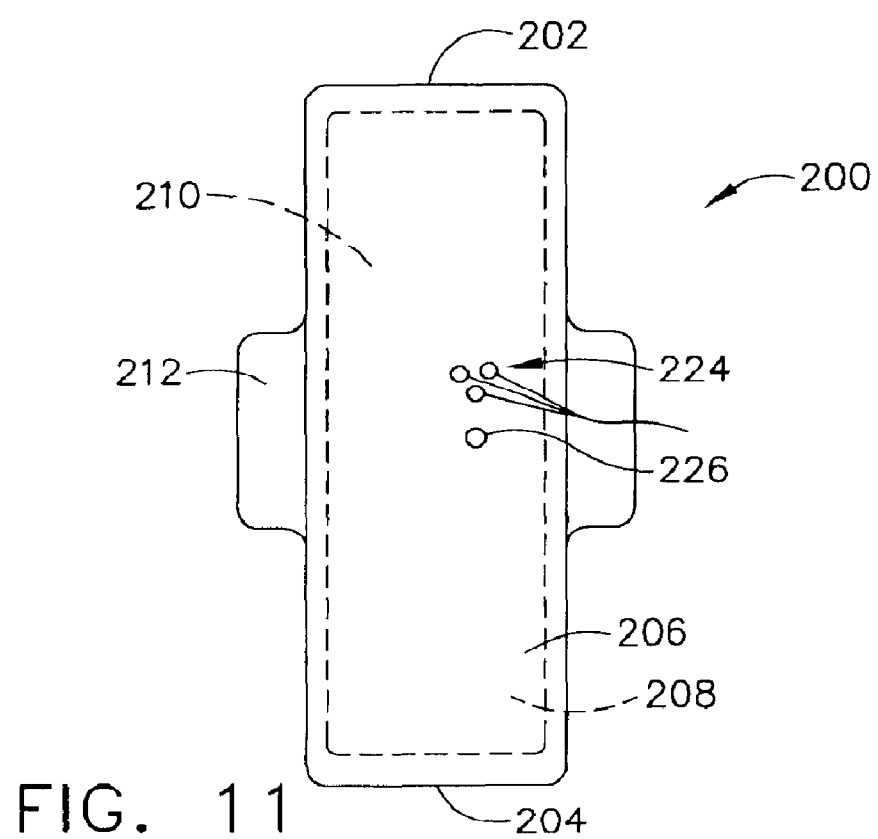
FIG. 11 is a plan view of the pad of FIG. 4 further comprising sensors operatively connected to the pad.

In another embodiment shown in FIG. 9, the absorbent article is a disposable fluid management device 650, such as a urine fluid management device, comprising a bag 652 having a flange 654 and an aperture 656. The bag typically comprises an adhesive layer 660. The aperture typically is surrounded by an adhesively faced flange for releasable attachment to the uro-genital area of the wearer. This disposable fluid management device is designed to acquire, absorb, and contain urine discharged from the body. The bags are typically liquid impermeable. The flange typically is adhered to the wearer's skin using skin friendly adhesive, however, with the diaper of this invention, the flange could be modified to removably affixed to the outside surface of diaper 20 of FIG. 17 using adhesive material. Alternately, the absorbent article 650 could comprise specially designed wings that either attach around the diaper side elastics as is typically done with pads, or could be removably attached to the body side of diaper 20 through opening 84.

Figure 8:
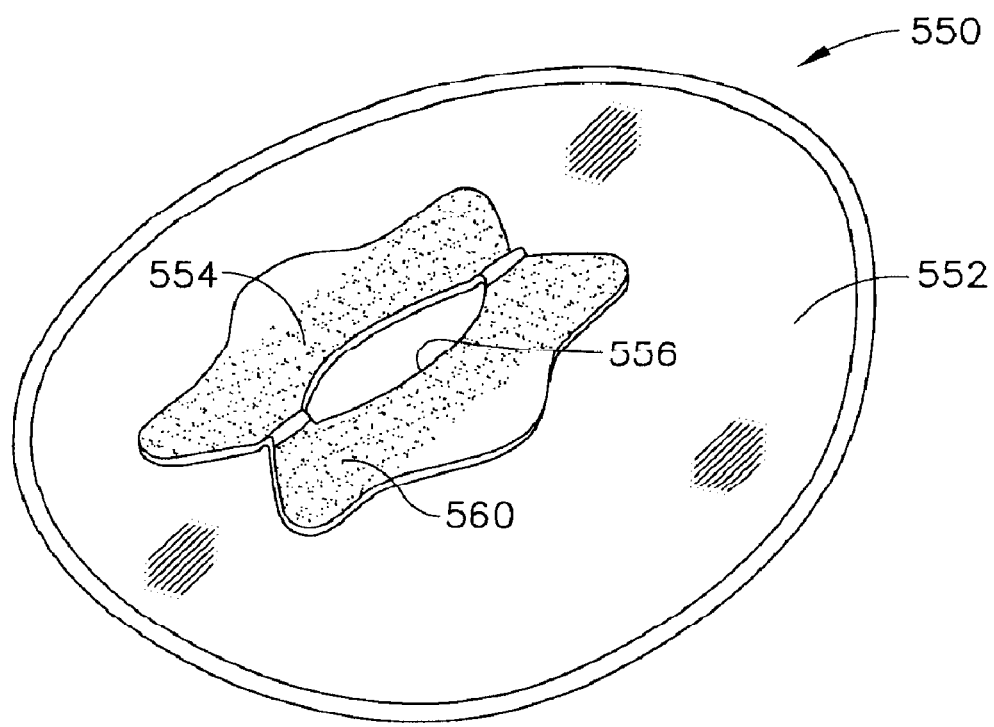
FIG. 8 is a plan view of an absorbent article BM management device suitable for use with a diaper herein.

In another embodiment shown in FIG. 8, such as described in U.S. Pat. No. 6,602,233 Palumbo, et al., the absorbent article is a disposable BM management device 550, comprising a bag 552 having a flange 554 and an aperture 556. The bag typically comprises an adhesive layer 560 for releasable attachment to the anal area of the wearer. This disposable BM management device is specifically designed to acquire, and contain feces discharged from the body. The flange typically is adhered to the wearer's skin using skin friendly adhesive 560. However, with the diaper of this invention, the flange could be modified to removably affixed to the outside surface of diaper 20 of FIG. 17 using adhesive material. Alternately, the BM management device 550 could comprise specially designed wings that could be removably attached to the body side of diaper 20 through opening 80.

Other well know BM absorbent devices, such as the BM containment system described in U.S. Pat. No. 6,346,097, Blaney, incorporated herein by reference, are also suitable for use with the diaper of this invention.

Figure 12:
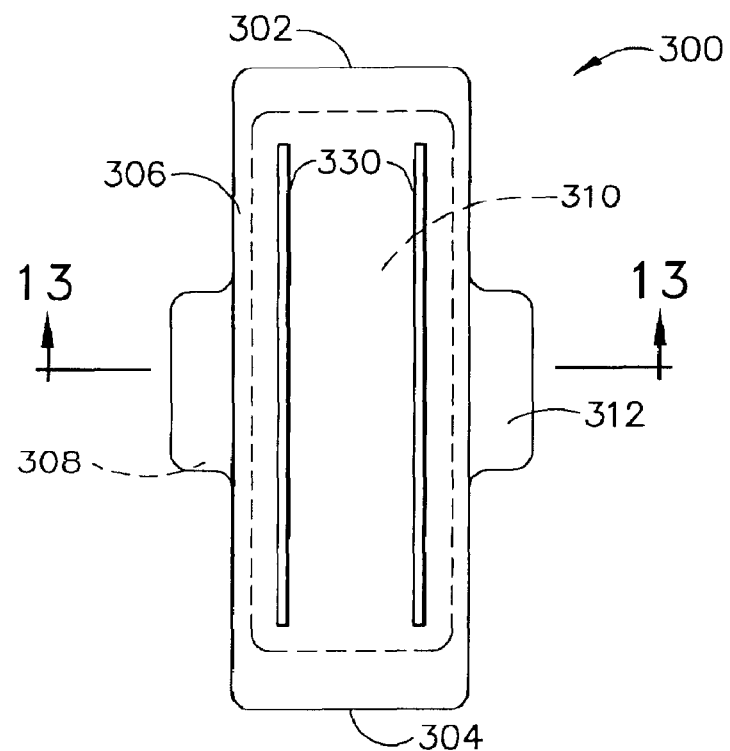
FIG. 12 is a plan view of the pad of FIG. 4 further comprising a pair of side shields.
Figure 13:
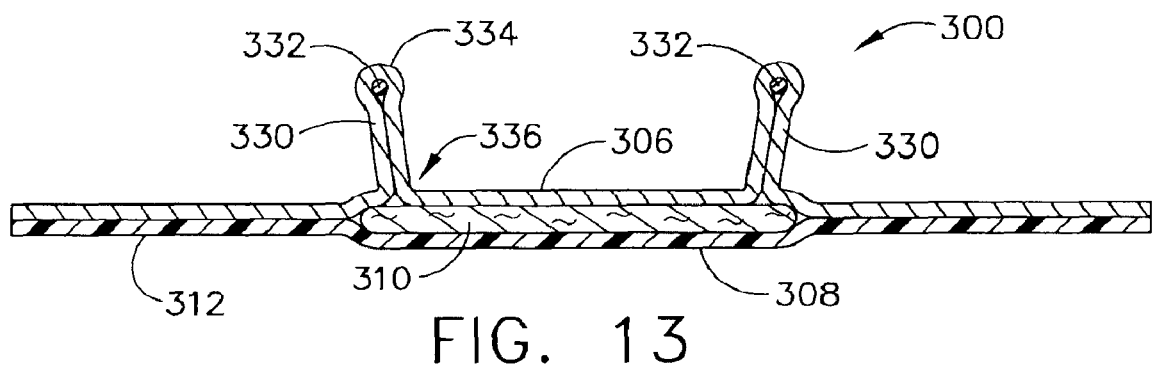
FIG. 13 is a sectional view of the pad of FIG. 12 taken along line 13-13.

One absorbent article useful herein comprises elasticized side shields, such as described in U.S. Pat. No. 6,773,424, Heyrman, et al., incorporated herein by reference. In one embodiment shown in FIGS. 12 and 13, a pair of side shields 330 are formed on opposite sides of the absorbent pad of FIG. 4 by a first elastic member 332 adjacent the first side of the pad and a second elastic member 332 adjacent the second side of the pad, the first and second elastic members contracting at least a portion of the first and second sides. Each of the side shields has an upstanding end 334 and a terminal end 336 adjacent the absorbent core 310 of the pad. The side shields may be formed by an extension of the topsheet, such topsheet 306 as shown in FIG. 13, in which event the side shields would typically be glued along their terminal ends 336. Alternatively, the side shields may be formed as separate elements that are attached to the topsheet, such as by gluing them to the topsheet. The side shields may extend the entire length of the pad or they may be shorter such as shown in FIG. 12, in which event they typically would be formed as separate elements that are attached to the topsheet. Other well know barrier leg cuff designs are also well suited for incorporation on absorbent articles used with the diaper of this invention.

Figure 14:
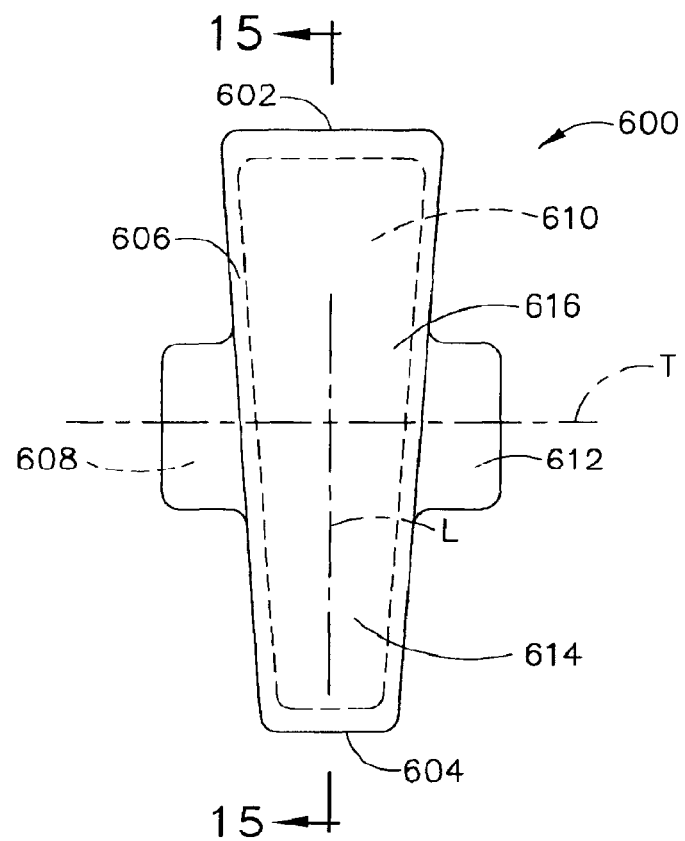
FIG. 14 is a plan view of an absorbent article herein with profiled absorbency suitable for use with a diaper of the invention.
Figure 15:
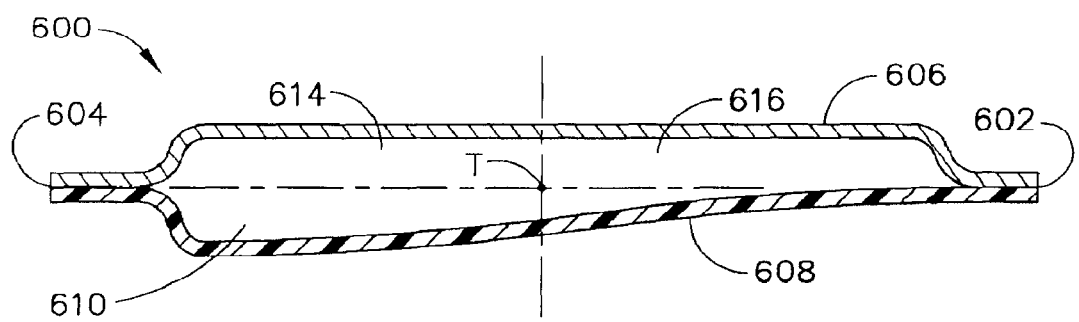
FIG. 15 is an enlarged sectional view of the article of FIG. 14 taken along line 15-15.

Another compatible absorbent article comprises a trapezoid-shaped primary absorbent core with profiled absorbency, such as shown in FIGS. 14 and 15. In one embodiment, the article is a thick incontinence pad comprising a trapezoid-shaped primary absorbent core with capacity great enough to handle medium to heavy urine flow. In the embodiment shown in FIG. 14, incontinence pad 600 comprises front edge 602, rear edge 604, and adjoining side edges that together form the periphery of the pad. The pad has a longitudinal centerline L and a lateral centerline T, which defines a rear region 614 and a front region 616 of the pad. The pad typically is symmetric about the longitudinal centerline L and asymmetric about the lateral centerline T. The pad also comprises a liquid pervious side such as a topsheet 606, a liquid impervious side such as backsheet 608, and a primary absorbent core such as absorbent core 610 that has a generally trapezoid shape, with substantially straight side edges that taper to a narrowed width near the rear edge 604. The liquid pervious side and the liquid impervious side are arranged to form a unitary structure. In FIG. 15, the lateral centerline T coincides with the lateral centerline of the primary absorbent core 610. In other embodiments, the primary absorbent core may be shifted up or down along the longitudinal centerline of the article. In pad 600, the primary absorbent core 610 has a length of about 21.0 cm, a width near the front edge 602 of the pad of about 6.5 cm, and a width near the rear edge 604 of the pad of about 2.2 cm. The primary absorbent core also typically has a width that is less than the width of the crotch region of the diaper. The pad thus has a size and shape compatible with the diaper so that it can be held in close bodily contact in the crotch region.

The pad 600 also comprises two side wings 612 that extend laterally from the central portion of the pad. The wings can be folded around the edges of the diaper in the crotch region to help stabilize the pad and prevent it from shifting out of place. The wings typically have a fastening system such as an adhesive or other attachment means to help secure them to the outer surface of the diaper in the crotch region. Wings 612 typically have a length at least about 75% of the length of the article. Such long wings improve the stability of the pad, and since they cover more of the diaper, better protect it and outer garments from soiling. The article may also comprise a pair of side shields on opposite sides of the pad, such as side shields 330 shown in FIGS. 12 and 13. The pad typically comprises, from the body surface down, a nonwoven or high-loft fibrous material topsheet, an airfelt and superabsorbent primary core, and a barrier backsheet.

Typically, the width of the primary absorbent core of a trapezoid-shaped article narrows rearwardly so it will fit effectively within the low motion zone of the crotch and between the wearer's buttocks. In conventional articles, as the primary absorbent core narrows, the absorbent capacity per unit area of core (i.e., capacity density) remains constant, resulting in the article having less total capacity in the rear half region of the article than in the front half region. This reduced total capacity in the rear region often leads to leakage, especially when the quantity of fluid (e.g., urine) to be absorbed exceeds the absorbent capacity in that region. In one embodiment of this invention, as the primary absorbent core narrows rearwardly, the capacity density of the primary core in the rear region is increased, e.g., proportionately increased, to maintain at least equal absorbent capacity in the rear region versus the front region of the article, i.e., the ratio of the absorbent capacity in the rear region to the absorbent capacity in the front region is at least about 1.0. In other embodiments, this ratio is at least about 1.2 and typically at least about 1.4, e.g., at least about 1.5. This increase in capacity density is often accomplished by adding more absorbent core material (e.g., airfelt and superabsorbent material) to the narrowed primary core. This added core material typically increases the thickness of the core in the rear region, thus creating a caliper profile along the longitudinal centerline L such that the caliper of the rear region 614 is greater than that of the front region 616. The pad thus typically has both an absorbent capacity profile and caliper profile in the longitudinal direction.

In one embodiment, the pad 600 has an absorbent capacity, as defined herein, of at least about 8.0 grams of fluid, typically at least about 20.0 grams of fluid, more typically at least about 40.0 grams of fluid, and yet more typically at least about 80.0 grams of fluid. The rear region 614 (e.g., rear 50% of the article) typically has an absorbent capacity equal to or greater than the absorbent capacity in the front region 616 (e.g., front 50% of the article). As a result, the rear region often has an absorbent capacity of at least about 4.0 grams of fluid, typically at least about 10.0 grams of fluid, more typically at least about 20.0 grams of fluid, and yet more typically at least about 40.0 grams of fluid. The front region of the pad typically has a caliper of greater than about 5.0 mm, more typically greater than about 7.0 mm, e.g., greater than about 10.0 mm. The performance of such a profiled pad is enhanced when it is held close to the fluid source and in close bodily contact by the diaper of this invention.

In one embodiment, articles useful herein comprise a lotion coating, a skin care composition, or a therapeutic composition that is at least partially transferable to the wearer's skin, such as described in U.S. Pat. No. 6,290,979, Roe, et al.; U.S. Pat. No. 6,156,024, Schulte, et al.; U.S. Pat. No. 5,609,587, Roe; U.S. Pat. No. 5,607,760, Roe; all incorporated herein by reference. The diaper maintains the article comprising the lotion, skin care composition or therapeutic composition in close bodily contact in the crotch region, and thus provides improved transfer of the lotion, skin care composition or therapeutic composition to the skin. The article may comprise one or more absorbent components or may be void of any absorbent component. The article has a body-contacting surface such as the topsheet described above and a diaper-contacting surface such as the backsheet described above, although in this article the topsheet need not be liquid pervious and the backsheet need not be liquid impervious. The lotion, skin care composition, or therapeutic composition is transferable to the wearer's skin in an effective amount to provide a skin health benefit or other therapeutic or health benefit.

One embodiment, such as described in U.S. Pat. No. 5,607,760, Roe, relates to an article having a lotion coating on the outer surface oriented toward the skin of the wearer, wherein at least a portion of the body-contacting surface of the article comprises a lotion coating which is solid or semi-solid at 20° C. and which is partially transferable to the wearer's skin. The lotion typically comprises: (i) from about 5 to about 95% of a substantially water free emollient having a plastic or fluid consistency at 20° C. and comprising a member selected from the group consisting of petroleum based emollients, fatty acid ester emollients, alkyl ethoxylate emollients, polysiloxane emollients, silicone wax emollients, and mixtures thereof; (ii) from about 5% to about 95% of an agent capable of immobilizing said emollient on the outer surface of the body-contacting surface, said immobilizing agent having a melting point of at least 35° C. and comprising a solid polyol polyester comprising a polyhydric alcohol containing at least 4 hydroxyl groups esterified with fatty acid or other organic radicals having from about 2 to about 30 carbon atoms. The quantity of lotion coating on at least a portion of the body-contacting surface typically ranges from about 0.1 mg/in$^2$ to about 25 mg/in$^2$, more typically from about 1 mg/in$^2$ to about 10 mg/in$^2$. Such lotioned articles provide therapeutic and/or protective lotion coating benefits. Because the emollient is substantially immobilized on the surface of the article, less lotion composition is needed to impart the desired benefits. Importantly, the lotion is easily transferable to the skin by way of normal contact, wearer motion, and/or body heat.

Another embodiment, such as described in U.S. Pat. No. 6,290,979, Roe et al., relates to an absorbent article having two or more skin care compositions disposed thereon. The skin care compositions, such as the lotions described above, may have different formulations such that the article can be designed to deliver specific skin care benefits to specific portions of the skin of the user. In one embodiment shown in FIG. 10, the absorbent pad of FIG. 4 further comprises a first region such as region 220 and a second region such as region 222. The first region has a first skin care composition disposed thereon that is semi-solid or solid at 20° C. and partially transferable to a wearer's skin. The second region has a second skin care composition disposed thereon that is semi-solid or solid at 20° C. and partially transferable to a wearer's skin. The first skin care composition has a different formulation than the second skin care composition. The first skin care composition is disposed in an effective amount to provide a first skin health benefit and the second skin care composition is disposed in an effective amount to provide a second skin health benefit. Alternatively, regions 220 and 222 may comprise the same or different lotions, skin care compositions, or therapeutic compositions, which are at least partially transferable to the wearer's skin.

The diaper of this invention can also be used with an article capable of being held in close bodily contact in the crotch region by the diaper, and comprising a sensor that is operatively connected to the article. The sensor is capable of detecting various target entities, including inputs that correlate to elimination of bodily wastes, biological analytes, etc., such as described in U.S. Pat. No. 6,570,053, Roe, et al.; and U.S. Pat. No. 6,713,660, Roe, et al.; both incorporated herein by reference. The diaper maintains the article in close bodily contact in the crotch region and thus provides improved sensor performance.

One embodiment, such as described in U.S. Pat. No. 6,570, 053, Roe, et al., relates to an article that predicts the occurrence of an event related to bodily waste, the wearer, the article, or a component or components thereof using a proactive sensor, and responds to this prediction by performing a function on the article or the wearer to prepare for or to delay the occurrence of the predicted event, or by signaling the caretaker or the wearer that the event is about to occur. Such a sensor could also signal that an event has occurred. The article typically comprises a sensor operatively connected to the article, the sensor being capable of detecting an input that correlates to elimination of bodily waste from the wearer; and means for signaling elimination of bodily waste. In one embodiment shown in FIG. 11, the absorbent pad of FIG. 4 further comprises such a sensor 224. The sensor may be integral with or separate from the article. The elimination of bodily waste may include urination, discharge of menses, or defecation. The input may be a change in pressure, an electrical signal, or a motion, or combinations thereof. The article may or may not be disposable, and may or may not comprise an absorbent component.

Another embodiment, such as described in U.S. Pat. No. 6,713,660, Roe, et al, relates to an article that comprises a biosensor including at least one bio-recognition element and a transducer. The biosensor is adapted to detect a target biological analyte in bodily waste or on the wearer's skin. The article may comprise a biosensor adapted to detect one or more specific microorganisms and/or related biomolecules and to signal the caretaker, the wearer, or an actuator of the occurrence. The bio-recognition element may comprise a biologically reactive agent, typically selected from the groups consisting of an enzyme or sequence of enzymes; an antibody; DNA; an organelle; a membrane receptor protein; a natural or synthetic cell membrane; viable or nonviable bacterial, plant, or animal cells; at least a portion of a nerve bundle; and at least a portion of a sensing organ; and combinations thereof. The bio-recognition element may be *Acinetobacter baumannii* TOI36 and *Bacillus* sp TOI41. The biosensor is typically a biocatalytic biosensor or a bioaffinity biosensor. The bioaffinity biosensor may be a chemoreceptor-based biosensor and an immunosensor. The biosensor may detect target biological analytes selected from the group consisting of pathogenic bacteria, colonic bacteria, viruses, parasites, bacterial toxins, fungi, enzymes, and combinations thereof. The biosensor may also detect target biological analytes associated with a systemic or skin health condition in the wearer prior to the onset of clinically observable symptoms of the condition. The biosensor typically detects the target biological analyte only above a pre-defined threshold level. In one embodiment shown in FIG. 11, the absorbent pad of FIG. 4 further comprises such a biosensor 226. The absorbent article may or may not be disposable, and may or may not comprise an absorbent component.

Test Method for Measuring the Crotch Holding Force (CHF) of a Material Using A "Constant-Rate-of-Extension (CRE) Ball Force Test"

Overview: This method measures a force (CHF) that is related to the holding force exerted by an extensible material when holding an article against a wearer's body.

Terminology: The Crotch Holding Force (CHF) is the force exerted by a material when distending it with a force applied at right angles to the plane of the material, under the specified conditions. The angle of application of force and the area of the material upon which the force is applied varies continuously as the material stretches when tested as directed in this method. In the Constant-Rate-of-Extension (CRE) tensile testing machine, the rate of increase of the specimen length is uniform with time.

Summary of Test Method: Set up the tensile testing machine for performing this test in accordance with both the manufacture's instructions and procedures presented herein. A specimen of material is securely clamped without tension within a "Ball Burst Test" attachment. A force is exerted against the specimen by a polished, hardened steel ball attached to the tensile testing machine. Crotch Holding Force (CHF) data are recorded as a function of extension distance.

Apparatus: Tensile testing machine, of the constant-rate-of-extension (CRE) type. Equipment includes an Imada DPZ High Performance Programmable Digital Force Gauge: Model DPZ-4, and an Imada Motorized Vertical Test Stand: Model MX-110-S Test Stand w/Digital Distance Meter, both available from Imada, Incorporated, Northbrook, Ill. The Force Ball Attachment (a modified "Ball Burst Test" attachment) consists of a clamping mechanism to hold the specimen and a steel ball attached to the moveable force gauge of the tensile testing machine. The circular opening and ring clamp have an internal diameter of 5.1 cm (2.0 in). The polished steel ball connected to the force gauge has a diameter of 1.6 cm (0.62 in).

Sampling and Specimen Preparation: The specimen is taken from the crotch region of the diaper. Clamp the specimen in the ring clamp of the apparatus. The specimen must be of sufficient diameter to be held securely within the 5.1 cm (2.0 in) diameter ring clamp. The specimen may not require cutting if there is ample room to securely clamp the specimen in the apparatus. Ensure the specimen is free of folds, creases, or wrinkles, and is without tension when clamped. If the specimen is not uniform (e.g., it has a pattern, stitching, or a seam, etc.), ensure that the area tested is representative of the crotch region.

Procedure:

Place the specimen in the ring clamp, without tension, and fasten securely.

Move the Force Ball to a position immediately adjacent the specimen. Make sure there is no force applied to the ball by the specimen (CHF-0.0=0 kgf).

Set the distance meter to zero (0 cm elongation).

Start the CRE machine and maintain a speed of 25.4+/−10 cm/min (10.0+/−0.5 in/min). Continue that speed until the specimen is extended at least 6.5 cm (2.6 in) or until a force of at least 2.0 kgf (4.5 lbf) is reached.

While the CRE machine and Force Ball are elongating the specimen, record Crotch Holding Force and elongation data at 0.5 second intervals.

Create a standard stress/strain curve (Crotch Holding Force versus elongation distance) with the resulting data.

Determine Crotch Holding Force (CHF) at the appropriate elongation distances.

In the above method:
  CHF-0.0 is the force at 0 cm specimen elongation, i.e., the start of data collection. CHF-0.0 should be 0 kgf at 0 cm elongation.
  CHF-2.0 is the force (kgf) at 2.0 cm Force Ball extension distance.
  CHF-4.0 is the force (kgf) at 4.0 cm Force Ball extension distance.
  CHF-5.5 is the force (kgf) at 5.5 cm Force Ball extension distance.

Test Method for Measuring Caliper

A comparator gauge such as the Ames, Model 130 with dial indicator Model 482, available from the B. C. Ames, Company of Waltham, Mass. is needed. The comparator gauge should typically have a circular comparator foot, a weight of 10.0 grams and a contact surface of 5.16 square centimeters. The gauge is further provided with an 80.0 gram weight to provide a total of 0.25 psi pressure. The comparator gauge is zeroed. The weight is placed on the spindle extending above the comparator dial. The comparator foot is raised and the absorbent article, with any adhesive release paper being removed and the adhesive sprinkled with corn starch, is placed garment surface down on the base plate. The absorbent article is positioned on the base plate so that when the foot is lowered, it is in the region of the absorbent article for which the measurement is desired. Try to smooth out or avoid any wrinkles. Gently lower the foot onto the absorbent article. Determine the caliper by reading the comparator dial 30 seconds after the foot comes in contact with the surface.

Test Method for Measuring Absorbent Capacity

The capacity of an absorbent article is determined as follows. Any adhesive release paper is removed from the absorbent article to be tested. To determine absorbent capacity, a sample comprising the entire absorbent article minus any release paper is obtained. The sample is weighed to the nearest 0.1 gram. The sample is then submerged in a beaker of 1% sterile saline (obtainable from the Baxter Travenol Company of Deerfield, Ill.), such that the sample is totally submerged and is not bent or otherwise twisted or folded. The sample is submerged for 10 minutes. The sample is removed from the saline and suspended for two minutes in a vertical position to allow the saline to drain out of the sample. The sample is then placed body-contacting surface down onto an absorbent blotter, such as the filter paper #631 available from the Filtration Science Corp., Eaton-Dikeman Division of Mount Holly Springs, Pa. A uniform 17.6 gram per square centimeter load is placed over the sample to squeeze excess fluid out. The absorbent blotter is replaced every 30 seconds until the amount of fluid transferred to the absorbent blotter is less than 0.5 grams in a 30 second period. Next, the sample is weighed to the nearest 0.1 gram and the dry weight of the sample is subtracted. The difference in grams is the absorbent capacity of the absorbent article.

All limits and ranges specified herein include all narrower ranges, limits, and amounts that are within the specified limits and ranges, and such narrower ranges and limits may be claimed even though those limits and ranges are not separately listed.

While particular embodiments of the present invention have been illustrated and described, various other changes and modifications can be made without departing from the spirit and scope of the invention. It is therefore intended to cover all such changes and modifications that are within the scope of this invention.

What is claimed is:

1. A diaper for holding an absorbent article in close bodily contact in the crotch region, said diaper having a longitudinal centerline defining a longitudinal direction and a lateral centerline defining a lateral direction, said diaper comprising:
  a) a front region;
  b) a crotch region attached to the front region, said crotch region comprising elastic material suitable for use in a diaper, said crotch region having high stretch in both the lateral and longitudinal directions as measured by having a Crotch Holding Force (CHF-4.0) of greater than about 0.1 kgf and a Crotch Holding Force (CHF-2.0) of less than about 1.0 kgf; and
  c) a rear region attached to the crotch region, said rear region comprising at least two fastening systems that cooperate with the front region to provide an adjustable waistband;
wherein when said diaper is used with an absorbent article, said crotch region holds the absorbent article in close bodily contact in the crotch region of the wearer.

2. The diaper according to claim 1 wherein the crotch region comprises knit material and elastomeric fiber material.

3. The diaper according to claim 1 that is reusable.

4. The diaper according to claim 1 further comprising side elastics.

5. The diaper according to claim 1 wherein the crotch region has a Crotch Holding Force (CHF-2.0) of less than about 0.6 kgf.

6. The diaper according to claim 1 wherein the crotch region has a Crotch Holding Force (CHF-4.0) of less than about 1.0 kgf.

7. The diaper according to claim 1 wherein the crotch region has a Crotch Holding Force (CHF-4.0) of less than about 0.8 kgf.

8. The diaper according to claim 1 wherein the crotch region has a Crotch Holding Force (CHF-5.5) of less than about 1.0 kgf.

9. The diaper according to claim 1 further comprising at least one extension or panel extending beyond the front, crotch, or rear region.

10. A diaper for holding an absorbent article in close bodily contact in the crotch region, said diaper having a longitudinal centerline defining a longitudinal direction and a lateral centerline defining a lateral direction, said diaper comprising:
  a) a front region;
  b) a crotch region attached to the front region, said crotch region comprising elastic material suitable for use in a diaper, said crotch region having high stretch in both the lateral and longitudinal directions as measured by having a Crotch Holding Force (CHF-4.0) of greater than about 0.1 kgf and a Crotch Holding Force (CHF-2.0) of less than about 0.6 kgf; and
  c) a rear region attached to the crotch region, said rear region comprising at least two fastening systems that cooperate with the front region to provide an adjustable waistband;

wherein when said diaper is used with an absorbent article, said crotch region holds the absorbent article in close bodily contact in the crotch region of the wearer.

11. The diaper according to claim 10 wherein the crotch region comprises knit material and elastomeric fiber material.

12. The diaper according to claim 10 that is reusable.

13. The diaper according to claim 10 further comprising side elastics.

14. The diaper according to claim 10 wherein the crotch region has a Crotch Holding Force (CHF-4.0) of less than about 1.0 kgf.

15. The diaper according to claim 10 wherein the crotch region has a Crotch Holding Force (CHF-4.0) of less than about 0.8 kgf.

16. The diaper according to claim 10 wherein the crotch region has a Crotch Holding Force (CHF-5.5) of less than about 1.0 kgf.

17. The diaper according to claim 10 further comprising at least one extension or panel extending beyond the front, crotch, or rear region.

18. A diaper for holding an absorbent article in close bodily contact in the crotch region, said diaper having a longitudinal centerline defining a longitudinal direction and a lateral centerline defining a lateral direction, said diaper comprising:
   1) a front region;
   2) a crotch region attached to the front region, said crotch region having at least one opening located either at the anus of an individual when the article is worn or at the urethral opening when the article is worn, and comprising elastic material suitable for use in a diaper, said crotch region having high stretch in both the lateral and longitudinal directions as measured by having a Crotch Holding Force (CHF-4.0) of greater than about 0.1 kgf and a Crotch Holding Force (CHF-2.0) of less than about 1.0 kgf; and
   3) a rear region attached to the crotch region, said rear region capable of cooperating with the front region to provide an adjustable waistband;

wherein when said diaper is used with an absorbent article, said crotch region holds the absorbent article in close bodily contact in the crotch region of the wearer.

19. The diaper according to claim 18 wherein the crotch region comprises knit material and elastomeric fiber material.

20. The diaper according to claim 18 that is reusable.

21. The diaper according to claim 18 further comprising elastics around the periphery of the at least one opening.

22. The diaper according to claim 18 further comprising at least one flap or pocket.

23. The diaper according to claim 18 wherein the crotch region has a Crotch Holding Force (CHF-2.0) of less than about 0.6 kgf.

24. The diaper according to claim 18 wherein the crotch region has a Crotch Holding Force (CHF-4.0) of less than about 1.0 kgf.

25. The diaper according to claim 18 wherein the crotch region has a Crotch Holding Force (CHF-4.0) of less than about 0.8 kgf.

26. The diaper according to claim 18 wherein the crotch region has a Crotch Holding Force (CHF-5.5) of less than about 1.0 kgf.

27. The diaper according to claim 18 further comprising at least two fastening systems attached to the rear region that cooperate with the front region to provide an adjustable waistband.

* * * * *